US009416169B2

(12) United States Patent
Marasco et al.

(10) Patent No.: US 9,416,169 B2
(45) Date of Patent: Aug. 16, 2016

(54) HUMANIZED MONOCLONAL ANTIBODIES AND METHODS OF USE

(71) Applicants: DANA-FARBER CANCER INSTITUTE, INC., Boston, MA (US); THE BRIGHAM AND WOMEN'S HOSPITAL, Boston, MA (US)

(72) Inventors: Wayne Marasco, Wellesley, MA (US); Jianhua Sui, Waltham, MA (US); Quan Zhu, Needham, MA (US); Thomas Kupper, Belmont, MA (US)

(73) Assignees: Dana-Farber Cancer Institute, Inc., Boston, MA (US); The Brigham and Women's Hospital, Boston, MA (US)

(*) Notice: Subject to any disclaimer, the term of this patent is extended or adjusted under 35 U.S.C. 154(b) by 29 days.

(21) Appl. No.: 14/597,044

(22) Filed: Jan. 14, 2015

(65) Prior Publication Data
US 2016/0176985 A1    Jun. 23, 2016

Related U.S. Application Data

(62) Division of application No. 12/810,888, filed as application No. PCT/US2008/088435 on Dec. 29, 2008, now Pat. No. 8,962,806.

(60) Provisional application No. 61/017,494, filed on Dec. 28, 2007.

(51) Int. Cl.
  A61K 39/395    (2006.01)
  C07K 14/715    (2006.01)
  C07K 16/28     (2006.01)

(52) U.S. Cl.
  CPC ......... *C07K 14/7158* (2013.01); *C07K 16/2866* (2013.01); *C07K 2316/96* (2013.01); *C07K 2317/24* (2013.01); *C07K 2317/56* (2013.01); *C07K 2317/565* (2013.01); *C07K 2317/73* (2013.01); *C07K 2317/732* (2013.01); *C07K 2317/734* (2013.01); *C07K 2317/74* (2013.01); *C07K 2317/76* (2013.01); *C07K 2317/92* (2013.01); *C07K 2319/30* (2013.01)

(58) Field of Classification Search
  CPC ........... A61K 39/395; A61K 39/39533; A61K 39/39558
  See application file for complete search history.

(56) References Cited

PUBLICATIONS

Baribaud et al. "Antigenically Distinct Conformations of CXCR4." *J. Virol.* 75.19(2001):8957-8967.
Boon et al. "Preclinical Assessment of Anti-CD40 Mab 5D12 in Cynomolgus Monkeys." *Toxicology*. 174.1(2002):53-65.
Campbell et al. "6-C-kine (SLC), a Lymphocyte Adhesion-Triggering Chemokine Expressed by High Endothelium, is an Agonist for the MIP-3β Receptor CCR7." *J. Cell. Biol.* 141.4(1998):1053-1059.
Campbell et al. "Biology of Chemokine and Classical Chemoattractant Receptors: Differential Requirements for Adhesion-Triggering Versus Chemotactic Responses in Lymphoid Cells." *J. Cell. Biol.* 134.1(1996):255-266.
Campbell et al. "CCR7 Expression and Memory T Cell Diversity in Humans." *J. Immunol.* 166.2(2001):877-884.
Campbell et al. "The Chemokine Receptor CCR4 in Vascular Recognition by Cutaneous but not Intestinal Memory T Cells." *Nature*. 400.6746(1999):776-780.
Fang et al. "Stable Antibody Expression at Therapeutic Levels Using the 2A Peptide." *Nature Biotechnol.* 23(2005):584-590.
Casset, Biochemical and Biophysical Research Communications, 2003, vol. 307, pp. 198-205.
Chen, Journal of Molecular Biology, 1999, vol. 293, pp. 865-881.
Ferenczi et al. "Increased CCR4 Expression in Cutaneous T Cell Lymphoma." *J. Invest. Dermatol.* 119(2002):1405-1410.
Gao et al. "Novel Adeno-Associated Viruses from Rhesus Monkeys as Vectors for Human Gene Therapy." *Proc. Natl. Acad. Sci. USA*. 99.18(2002):11854-11859.
GenBank Accession No. ABG38372.1, Nov. 27, 2006.
Gussow, D., et al. "Humanization of Monoclonal Antibodies" in Methods of Enzymology, 203: 99-121, 1991.
Hendricks et al. "Alterations in Expression of Monocyte Chemotactic Protein-1 in the Simian Immunodeficiency Virus Model of Disseminated *Mycobacterium avium* Complex." *J. Infect. Dis.* 189.9(2004):1714-1720.
Hill et al. "The Amino Terminus of Human CCR5 is Required for its Function as a Receptor for Diverse Human and Simian Immunodeficiency Virus Envelope Glycoproteins." *Virology*. 248(1998):357-371.
Hirahara et al. "The Majority of Human Peripheral Blood CD4$^+$CD25$^{high}$Foxp3+ Regulatory T Cells Bear Functional Skin-Homing Receptors." *J. Immunol.* 177.7(2006):4488-4494.
Holm, Molecular Immunology, 2007, vol. 44, pp. 1075-1084.
Iellem et al. "Unique Chemotactic Response Profile and Specific Expression of Chemokine Receptors CCR4 and CCR8 by CD4$^+$ CD25$^+$ Regulatory T Cells." *J. Exp. Med.* 194.6(2001):847-853.
Ishida et al. "CCR4 as a Novel Molecular Target for Immunotherapy of Cancer." *Cancer Sci.* 97.11(2006):1139-1146.
Juremalm et al. "CCL17 and CCL22 Attenuate CCL5-Induced Mast Cell Migration." *Clin. Exp. Allergy*. 35.6(2005):708-712.
Kadin et al. "Systemic and Primary Cutaneous Anaplastic Large Cell Lymphomas." *Sem. Hematol.* 40.3(2003):244-256.
Karlsson et al. "Kinetic Analysis of Monoclonal Antibody-Antigen Interactions with a New Biosensor Based Analytical System." *J. Immunol. Methods*. 145.1-2(1991):229-240.
Kaufman et al. "Amiplification and Expression of Sequences Cotransfected with a Modular Dihydrofolate Reductase Complementary DNA Gene." *J. Mol. Biol.* 159.4(1982):601-621.

(Continued)

*Primary Examiner* — Alana Harris Dent
*Assistant Examiner* — Anne Holleran
(74) *Attorney, Agent, or Firm* — Cooley LLP; Ivor R. Elrifi; Cynthia A. Kozakiewicz

(57) ABSTRACT

The present invention comprises a humanized monoclonal antibody that binds to the chemokine receptor CCR4. This antibody is derived from Mab 1567 and recognizes the same epitope. Binding of the invented antibody to CCR4 inhibits ligand-mediated activities and is used to treat symptoms of cancer. Moreover, the antibody is used in combination with vaccines to suppress the activity of regulatory T cells.

18 Claims, 15 Drawing Sheets

(56) References Cited

PUBLICATIONS

Kim et al. "Long-Term Outcome of 525 Patients with Mycosis Fungoides and Sézary Syndrome: Clinical Prognostic Factors and Risk for Disease Progression." *Arch. Dematol.* 139(2003):857-866.

Kleinhans et al. "Functional Expression of the Eotaxin Receptor CCR3 in CD30+ Cutaneous T-Cell Lymphoma." *Blood.* 101.4(2003):1487-1493.

Kunkel et al. "Expression of the Chemokine Receptors CCR4, CCR5, and CXCR3 by Human Tissue-Infiltrating Lymphocytes." *Am. J. Pathol.* 160.1(2002):347-355.

Lee et al. "Epitope Mapping of CCR5 Reveals Multiple Conformational States and Distinct but Overlapping Structures Involved in Chemokine and Coreceptor Function." *J. Biol. Chem.* 274(1999):9617-9626.

Li et al. "Comparative Genome-Scale Analysis of Gene Expression Profiles in T Cell Lymphoma Cells During Malignant Progression Using a Complementary DNA Microarray." *Am. J. Pathol.* 158.4(2001):1231-1237.

Mansfield et al. "Induction of Disseminated *Mycobacterium avium* in Simian AIDS is Dependent upon Simian Immunodeficiency Virus Strain and Defective Granuloma Formation." *Am. J. Pathol.* 159.2(2001):693-702.

Marasco et al. "Therapeutic Antibody Gene Transfer." *Nature Biotechnol.* 23(2005):551-552.

Marks et al. "Antibody Affinity Maturation by Chain Shuffling." *Methods Mol. Biol.* 248(2004):327-343.

MacCallum, Journal of Molecular Biology, 1996, vol. 262, pp. 732-745.

Nakai et al. "Unrestricted Hepatocyte Transduction with Adeno-Associated Virus Serotype 8 Vectors in Mice." *J. Virol.* 79(2005):214-224.

Navratilova et al. "Analyzing Ligand and Small Molecule Binding Activity of Solubilized GPCRs Using Biosensor." *Anal. Biochem.* 355.1(2006):132-139.

Navratilova et al. "Solubilization, Stabilization, and Purification of Chemokine Receptors Using Biosensor Technology." *Anal. Biochem.* 339.2(2005):271-281.

Nimmerjahn et al. "Divergent Immunoglobulin G Subclass Activity Through Selective Fc Receptor Binding." *Science.* 310(2005):1510-1512.

Palmisano et al. "Expression of CTLA-4 in Nonhuman Primate Lymphocytes and its use as a Potential Target for Specific Immunotoxin-Mediated Apoptosis: Results of in vitro Studies." *Clin. Exp. Immunol.* 135.2(2004):259-266.

Pascalis, Journal of Immunology, 2002, Voo. 169, pp. 3076-3084.

Pfeifer et al. "A Murine Xenograft Model for Human CD30+ Anaplastic Large Cell Lymphoma: Successful Growth Inhibition with an Anti-CD30 Antibody (HeFi-1)." *Am. J. Pathol.* 155.4(1999):1353-1359.

Querfield et al. "The Spectrum of Cutaneous T-Cell Lymphomas: New Insight into Biology and Therapy." *Curr. Opin. Hematol.* 12.4(2005):273-278.

Rademacher et al. "Immunoglobulin G as a Glycoprotein." *Biochem. Soc. Symp.* 51(1986):131-148.

Reff et al. "Depletion of B Cells in vivo by a Chimeric Mouse Human Monoclonal Antibody to CD20." *Blood.* 83.2(Jan. 1994):435-445.

Robert et al. "Mechanisms of Disease: Inflammatory Skin Diseases, T Cells, and Immune Surveillance." *N. Eng. J. Med.* 341.24(1999):1817-1828.

Rudikoff et al. Proc. Natl Acad Sci, USA 1982, vol. 79, pp. 1979-1983, (1982).

Schier et al. "Efficient in vitro Affinity Maturation of Phage Antibodies Using BIAcore Guided Selections." *Hum. Antibodies Hybridomas.* 7.3(1996):97-105.

Shinkawa et al. "The Absence of Fucose but not the Presence of Galactose or Bisecting *N*-Acetylglucosamine of Human IgG1 Complex-Type Oligosaccharides Shows the Critical Role of Enhancing Antibody-Dependent Cellular Cytotoxicity." *J. Biol. Chem.* 278.5(2003):3466-3473.

Silber et al. "Recruitment of Lymphocytes During Cutaneous Delayed Hypersensitivity in Nonhuman Primates is Dependent on E-Selection and Vascular Cell Adhesion Molecule 1." *J. Clin. Invest.* 93.4(1994):1554-1563.

Soler et al. "CCR4 Versus CCR10 in Human Cutaneous $T_H$ Lymphocyte." *Blood.* 101.5(2003):1677-1682.

Stenlund et al. "Capture and Reconstitution of G Protein-Coupled Receptors on a Biosensor Surface." *Anal. Biochem.* 316.2(2003):243-250.

Vajdos, Journal of Molecular biology, 2002, vol. 320, pp. 415-428.

Vugmeyster et al. "Differential in vivo Effects of Rituximab on Two B-Cell Subsets in Cynomolgus Monkeys." *Int. Immunopharmacol.* 3.10-11(Oct. 2003):1477-1487.

Vugmeyster et al. "Effect of Anti-CD20 Monoclonal Antibody, Rituxan, on Cynomolgus Monkey and Human B Cells in a Whole Body Matrix." *Cytometry.* 52A(2003):101-109.

Warnock et al. "The Role of Chemokines in the Microenvironmental Control of T Versus B Cell Arrest in Peyer's Patch High Endothelial Venules." *J. Exp. Med.* 191(2000):77-88.

Willemze et al. "WHO-EORTC Classification for Cutaneous Lymphomas." *Blood.* 105(2005):3768-3785.

Wu, Journal of Molecular Biology, 1999, vol. 294, pp. 151-162.

Xiao et al. "Production of High-Titer Recombinant Adeno-Associated Virus Vectors in the Absence of Helper Adenovirus." *J. Virol.* 72.3(1998):2224-2232.

Yamanaka et al. "Decreased T-Cell Receptor Excision Circles in Cutaneous T-Cell Lymphoma." *Clin. Cancer Res.* 11.16(2005):5748-5755.

Yawalker et al. "Profound Loss of T-Cell Receptor Repertoire Complexity in Cutaneous T-Cell Lymphoma." *Blood.* 102.12(2003):4059-4066.

Zhang et al. "Activation of Jak/STAT Proteins Involved in Signal Transduction Pathway Mediated by Receptor for Interleukin 2 in Malignant T Lymphocytes Derived from Cutaneous Anaplastic Large T-Cell Lymphoma and Sezary Syndrome." *Proc. Natl. Acad. Sci. USA.* 93.17(1996):9148-9153.

Zola, H., et al. Journal of Immunological Methods, 319: 1-5, 2007; available online Dec. 6, 2006.

SEQUENCE LISTING

<160> NUMBER OF SEQ ID NOS: 15

<210> SEQ ID NO 1
<211> LENGTH: 354
<212> TYPE: DNA
<213> ORGANISM: Homo sapiens

<400> SEQUENCE: 1
caggtgcagc tggtgcagag cggagccgag gtgaagaagc ctggagcttc cgtcaaggtg     60
tcctgcaagg ccagcggcta caccttcgcc agctactaca tgcactggat gcggcaggca    120
cctggacagg gcctcgaatg gatcggctgg atcaaccccg gcaacgtgaa caccaagtac    180
aacgagaagt tcaagggcag ggccaccctg accgtggaca ccagcaccaa caccgcctac    240
atggaactga gcagcctgcg gagcgaggac accgccgtgt actactgcgc cagaagcacc    300
tactaccggc ccctggacta ctggggccag ggcaccctgg tgaccgtgag cagc          354

<210> SEQ ID NO 2
<211> LENGTH: 118
<212> TYPE: PRT
<213> ORGANISM: Homo sapiens

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Ser Tyr
            20                  25                  30

Tyr Met His Trp Met Arg Gln Ala Pro Gly Gln Gly Leu Glu Trp Ile
        35                  40                  45

Gly Trp Ile Asn Pro Gly Asn Val Asn Thr Lys Tyr Asn Glu Lys Phe
    50                  55                  60

Lys Gly Arg Ala Thr Leu Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Tyr Tyr Arg Pro Leu Asp Tyr Trp Gly Gln Gly Thr
            100                 105                 110

Leu Val Thr Val Ser Ser
        115

<210> SEQ ID NO 3
<211> LENGTH: 336
<212> TYPE: DNA
<213> ORGANISM: Homo sapiens

<400> SEQUENCE: 3
gacatcgtga tgacccagag ccccgacagc ctggccgtga gcctgggcga gcgggccacc     60
atcaactgca gagcagcca gagcatcctg tacagcagca accagaagaa ctacctggcc    120
tggtatcagc agaagcccgg ccagagcccc aagctgctga tctactgggc cagcacccgg    180
gagagcggcg tgcccgaccg gtttagcggc agcggctccg gcaccgactt cacccctgacc   240 atcagcagcc tgcaggccga ggacgtggcc gtgtactact gccaccagta cctgagcagc    300
tacaccttcg gccagggcac aaagctggaa atcaag                              336

<210> SEQ ID NO 4
<211> LENGTH: 112
<212> TYPE: PRT
<213> ORGANISM: Homo sapiens -continued

<400> SEQUENCE: 4

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Leu Ser Ser Tyr Thr Phe Gly Gln Gly Thr Lys Leu Glu Ile Lys
            100                 105                 110

<210> SEQ ID NO 5
<211> LENGTH: 8
<212> TYPE: PRT
<213> ORGANISM: Homo sapiens

<400> SEQUENCE: 5

Gly Tyr Thr Phe Ala Ser Tyr Tyr
1               5

<210> SEQ ID NO 6
<211> LENGTH: 17
<212> TYPE: PRT
<213> ORGANISM: Homo sapiens

<400> SEQUENCE: 6

Trp Ile Asn Pro Gly Asn Val Asn Thr Lys Tyr Asn Glu Lys Phe Lys
1               5                   10                  15

Gly

<210> SEQ ID NO 7
<211> LENGTH: 9
<212> TYPE: PRT
<213> ORGANISM: Homo sapiens

<400> SEQUENCE: 7

Ser Thr Tyr Tyr Arg Pro Leu Asp Tyr
1               5

<210> SEQ ID NO 8
<211> LENGTH: 17
<212> TYPE: PRT
<213> ORGANISM: Homo sapiens

<400> SEQUENCE: 8

Lys Ser Ser Gln Ser Ile Leu Tyr Ser Ser Asn Gln Lys Asn Tyr Leu
1               5                   10                  15

Ala

<210> SEQ ID NO 9
<211> LENGTH: 7
<212> TYPE: PRT
<213> ORGANISM: Homo sapiens

```
<400> SEQUENCE: 9

Trp Ala Ser Thr Arg Glu Ser
1               5

<210> SEQ ID NO 10
<211> LENGTH: 8
<212> TYPE: PRT
<213> ORGANISM: Homo sapiens

<400> SEQUENCE: 10

His Gln Tyr Leu Ser Ser Tyr Thr
1               5

<210> SEQ ID NO 11
<211> LENGTH: 17
<212> TYPE: PRT
<213> ORGANISM: Homo sapiens
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 11

Trp Ile Asn Xaa Xaa Asn Xaa Asn Xaa Lys Tyr Asn Glu Lys Phe Lys
1               5                   10                  15

Gly

<210> SEQ ID NO 12
<211> LENGTH: 9
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 12

Ser Xaa Tyr Xaa Xaa Pro Leu Asp Xaa
1               5

<210> SEQ ID NO 13
<211> LENGTH: 17
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (10)..(13)
<223> OTHER INFORMATION: Xaa can be any naturally occurring amino acid
```

```
<400> SEQUENCE: 13

Lys Ser Ser Gln Ser Xaa Leu Tyr Ser Xaa Xaa Xaa Xaa Asn Tyr Leu
1               5                   10                  15
Ala

<210> SEQ ID NO 14
<211> LENGTH: 7
<212> TYPE: PRT
<213> ORGANISM: Homo sapiens
<220> FEATURE:
<221> NAME/KEY: misc_feature
<222> LOCATION: (4)..(5)
<223> OTHER INFORMATION: Xaa can be any naturally occurring amino acid

<400> SEQUENCE: 14

Trp Ala Ser Xaa Xaa Glu Ser
1               5

<210> SEQ ID NO 15
<211> LENGTH: 8
<212> TYPE: PRT
<213> ORGANISM: Homo sapiens
<220> FEATURE:
<221> NAME/KEY: misc_feature
<222> LOCATION: (5)..(6)
<223> OTHER INFORMATION: Xaa can be any naturally occurring amino acid

<400> SEQUENCE: 15

His Gln Tyr Leu Xaa Xaa Tyr Thr
1               5
```

HUMANIZED MONOCLONAL ANTIBODIES AND METHODS OF USE

RELATED APPLICATIONS

This application is a divisional of U.S. patent application Ser. No. 12/810,888, filed Mar. 11, 2011, which is a national stage application, filed under 35 U.S.C §371, of International Patent Application No. PCT/US2008/088435, filed Dec. 29, 2008, which claims priority benefit of U.S. Provisional Patent Application No. 61/017,494, filed Dec. 28, 2007, the contents of which are herein incorporated by reference in-their entireties.

FIELD OF THE INVENTION

This invention relates generally to humanized anti-CCR4 antibodies as well as to methods for use thereof.

INCORPORATION-BY-REFERENCE OF SEQUENCE LISTING

The contents of the text file named "DFCI_048D01US_Sequence.txt", which was created on Jan. 13, 2015 and is 6.41 kilobytes in size, are hereby incorporated by reference in their entirety.

BACKGROUND OF THE INVENTION

Cutaneous T cell lymphomas (CTCLs) are the most common extranodal non-Hodgkin's T cell lymphomas in adults. A recent WHO-EORTC consensus classification (Willemze R. et al. Blood 2005, 105:3768-3785) indicates that there are thirteen clinically and histologically distinct types of CTCL; however, 90% of CTCLs fall into three classes: mycosis fungoides, primary cutaneous anaplastic large cell lymphoma, and Sezary syndrome. The most common type of CTCL, mycosis fungoides, is characterized by erythematous patches and plaques that most commonly contain CD4+ T cells that show an affinity for the epidermis, or epidermotropism (Willemze R. et al. Blood 2005, 105:3768-3785). Staging is based upon a TNM classification; patients with Stage 1A disease have normal life expectancies, while patients with Stage 1B or greater have a diminished life expectancy (Kim, Y. H. et al. Arch Dermatol 2003, 139:857-866). Patients with Stage II-IV disease have a median survival of less than five years, with large cell transformation often leading to accelerated deterioration (Kim, Y. H. et al. Arch Dermatol 2003, 139:857-866). Sezary syndrome is a leukemic variant of CTCL wherein clonal CD4+ T cells accumulate in blood and lymph nodes as well as skin; five year survival is less than 25%. Primary cutaneous ALCL has a much less aggressive course, with a five year survival of 95%; however, cutaneous ALCL with concurrent nodal involvement is more aggressive (Willemze R. et al. Blood 2005, 105:3768-3785; Kadin M E, Carpenter C. Semin Hematol 2003, 40:244-256).

There is significant immune dysfunction in these patients, with global dysregulation of the T cell repertoire of unknown etiology (Yamanaka K. et al. Clin Cancer Res 2005, 11:5748-5755; Yawalkar N. et al. Blood 2003, 102:4059-4066). The terminal event in most patients is bacterial sepsis. Current therapies for advanced MF and Sezary syndrome are palliative and durable long-term remissions are rare (Querfeld C. et al. Curr Opin Hematol 2005, 12:273-278). There is an urgent need for more effective therapies.

SUMMARY OF THE INVENTION

The invention is based upon the discovery of monoclonal antibodies which bind the CC-chemokine receptor 4 (CCR4). The monoclonal antibody is fully human. In various aspects, the monoclonal antibody is a bivalent antibody, a monovalent antibody, a single chain antibody or fragment thereof. Exemplary monoclonal antibodies include a monoclonal antibody that binds to the same epitope as murine 1567.

The monoclonal antibodies of the invention can have a binding affinity that is 1 $nM^{-1}$ or less. The monoclonal antibodies of the invention function to inhibit viral and cell membrane fusion.

The monoclonal antibody has a heavy chain variable amino acid sequence containing SEQ ID NOS: 2, and/or a light chain variable amino acid sequence containing SEQ ID NOS: 4. The monoclonal antibody has a heavy chain variable nucleic acid sequence containing SEQ ID NOS: 1, and/or a light chain variable nucleic acid sequence containing SEQ ID NOS: 3.

Also provided by the invention is an monoclonal anti-CCR4 protein antibody or fragment thereof, where the antibody has a $V_H$ CDR1 region having the amino acid sequence GYTFASYY; a $V_H$ CDR2 region having the amino acid sequence WINPGNVNTKYNEKFKG; a $V_H$ CDR3 region having the amino acid sequence STYYRPLDY; $V_L$ CDR1 region having amino acid sequence KSSQSILYSSNQK-NYLA; a $V_L$ CDR2 region having the amino acid sequence WASTRES and/or a $V_L$ CDR3 region having the amino acid sequence HQYLSSYT.

In another aspect, the invention provides a method of selectively killing a tumor cell, e.g. a T cell tumor, by contacting a cell with an anti-CCR4 antibody according to the invention. The selective killing occurs by antibody-dependent cellular toxicity (ADCC), complement-dependent cytotoxicity (CDC), or antibody dependent cellular.

Also included in the invention is a method of augmenting an immune response to an antigen, e.g. a viral antigen such as HIV, a bacterial antigen or a tumor associated antigen by contacting a cell with an anti-CCR4 antibody according to the invention. The antibody is administered prior to or after exposure to an antigen. The cell is a T-cell such as an effector T-cell.

DETAILED DESCRIPTION

Figure 1:
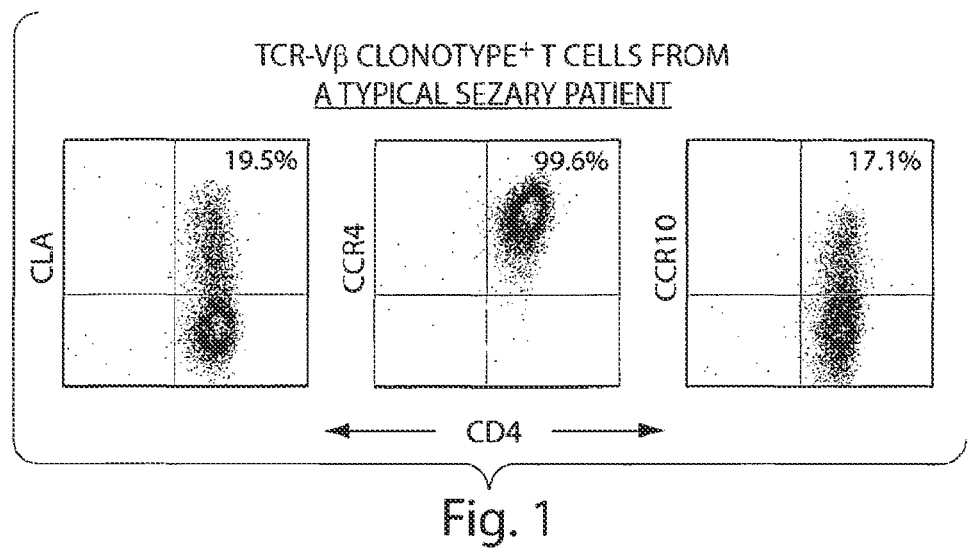
FIG. 1 are schematics showing Fluorescence Activated Cell Sorter (FACS) analysis of the expression of Cutaneous Lymphocyte Homing Receptors by CTCL cells identified by expanded TCR-Vβ-specific clone showing that CTCL clones from leukemic CTCL patients are enriched in the expression of homing receptors normally found only on cutaneous memory CD4 cells.

The present invention provides humanized monoclonal antibodies specific against chemokine (C—C motif) receptor 4 (CCR4). More specifically, the invention provides a therapeutic antibody that eliminates malignant CTCL cells while minimizing collateral damage to an already compromised immune system. The antibodies are respectively referred to herein is huCCR4 antibodies.

Cutaneous T-cell lymphomas (CTCLs) are a heterogenous group of lymphoproliferative disorders causes by clonally derived skin homing T cells. CTCL cells uniformly express CCR4. Specifically, CCR4 is a prominent feature of malignant T cells in MF, cutaneous ALCL, and roughly 50% of nodal ALCL. Unlike CLA, it is reliably expressed in Sezary syndrome and during large cell transformation of MF and is also expressed by other T lymphoid malignancies that can involve skin, such as Adult T Cell Leukemia/Lymphoma (ATLL). Expression of CCR4 is limited amongst non-malignant cells and absent on neutrophils, monocytes, or B cells. Importantly, CCR4 is absent on naïve T cells, and present on fewer than half of all memory T cells. The reliable expression of CCR4 on CTCL cells, and its limited expression on other immune cells, makes targeted therapy of CCR4 an attractive goal for these malignancies.

While some progress has been made in identifying small molecule inhibitors that are relatively selective for CCR4, specific monoclonal antibodies against CCR4 are an attractive target for immunotherapy of CTCL because of their exquisite binding specificity. In addition, the in vivo effector functions that are mediated through Fc binding to Fcγ receptors can be exploited to kill tumor cells. The precise properties of Mabs that are required for optimal in vivo immunodepleting activity are not known, but antibodies can be selected to act as either as receptor agonists or antagonists, and/or to promote or inhibit receptor dimerization and/or internalization. Different immune mechanisms of antibody-mediated tumor clearance have also been identified. For example, Mab-mediated recruitment of natural killer cells to tumors can occur through the Fc-γ activation of receptors on these immune effector cells, a process known as antibody-dependent cellular cytotoxicity (ADCC). Other immune mechanisms include complement dependent cytotoxcicity (CDC) and antibody dependent cellular phagocytosis (ADCP). Additional mechanisms related to intrinsic Mab activities include: blockade of ligand binding or hetero-dimerization, inhibition of downstream signaling of Akt, and acceleration of receptor internalization. The latter mechanism is particularly effective because ligand-induced endocytosis and degradation of active receptor tyrosine kinases (RTKs) is considered a major physiological process underlying attenuation of growth-promoting signals.

Leukocyte trafficking, which is critically regulated by chemokines and their receptors, share many of the characteristics of tumor cell infiltration and metastasis. While expression of the chemokine receptor CCR4 by tumor cells is associated with skin involvement, CCR4 also has an important role in both normal and tumor immunity. In a subset of CTCL patients with HTLV-1 associated Adult T-cell leukemia/lymphoma (ATLL), the tumor cells themselves function as regulatory T (Treg) cells, contributing to tumor survival in the face of host anti-tumor immune responses. In other types of cancers, the chemokines TARC/CCL17 and MDC/CCL22, specific ligands for CCR4 that are produced by tumor cells and the tumor microenvironment, attract $CCR4^+$ Treg cells to the tumor, where they create a favorable environment for tumor escape from host immune responses. Thus, a therapeutic anti-CCR4 Mab is the ideal treatment modality for many different cancers, not only to directly kill the $CCR4^+$ tumor cells, but also to overcome the suppressive effect of CCR4 Treg cells on the host immune response to tumor cells.

In one aspect the present invention provides a humanized monoclonal antibody that specifically binds CCR4 proteins. Binding of this antibody to the CCR4 receptor, interrupts ligand or agonist binding of CCR4. Exemplary ligands or agonists that compete for binding to the CCR4, and which are blocked in the presence of the invented antibody, include, but are not limited to, CCL17, CCL22, and vMIP-III. By a variety of mechanisms, the antibody decreases ligand-induced chemotaxis of cutaneous T cell lymphoma cells (CTCL cells). The huCCR4 antibody is monovalent or bivalent and comprise a single or double chain. Functionally, the binding affinity of the huCCR4 antibody is about 1 $nM^{-1}$ or less. The sequence of the antibody is engineered from and thus, may comprises one or more antigen-binding regions of murine CCR4 antibody 1567. The hCCR4 antibody binds the same epitope as murine CCR4 Mab 1567. The glycosylation of the Fc region of the antibody is modified to alter CCR4 binding or CCR4 ligand-blocking characteristics. For instance, the fucose content of the Fc region is decreased compared to wild type. Furthermore, the antibody comprises a therapeutic agent including, but not limited to, a toxin, a radiolabel, a siRNA, or a cytokine.

The huCCR4 antibody is capable of inducing cell death. Cell death is induced by either direct or indirect mechanisms. For example, the huCCr4 antibody binds CCR4 expressed on the surface of the target cell and leads to the death of that CCR4-expressing cell via intracellular signaling pathways. For instance, CCR4 binding by the huCCR4 antibody can lead to complement-dependent cytotoxicity (CDC). Alternatively, the huCCR4 antibody binds CCR4, and leads to the recruitment of a second cell type that will kill the CCR4-expressing target cell. Exemplary mechanisms by which the huCCR4 antibody mediates cell death by recruitment of a second cell type include, but are not limited to, antibody-dependent cellular toxicity (ADCC) and antibody dependent cellular phagocytosis (ADCP). Target CCR4-expressing cell types comprise tumor and regulatory, or supplementary, T cells (also referred to as Treg cells).

The heavy chain CDRs of the huCCR4 antibody have the following sequences: CDRH1: GYTFASYY (SEQ ID NO:5); CDRH2: WINPGNVNTKYNEKFKG (SEQ ID NO:6); and CDRH3: STYYRPLDY (SEQ ID NO:7). The light chain CDRs of the huCCR4 antibody have the following sequences: CDRL1: KSSQSILYSSNQKNYLA (SEQ ID NO:8); CDRL2: WASTRES (SEQ ID NO:9); and CDRL3: HQYLSSYT (SEQ ID NO:10).

huCCR4 VH nucleotide sequence: (SEQ ID NO: 1) CAG-GTGCAGCTGGTGCAGAGCGGAGCCGAGGTGAAGA-AGCCTGGAGCTTCCGTCAAGGTGTCCTGCAAGGC-CAGCGGCTACACCTTCGCCAGCTACTACATGCACT-GGATGCGGCAGGCACCTGGACAGGGCCTCGAATG-GATCGGCTGGATCAACCCCGGCAACGTGAACACC-AAGTACAACGAGAAGTTCAAGGGCAGGGCCACCC-TGACCGTGGACACCAGCACCAACACCGCCTACATG-GAACTGAGCAGCCTGCGGAGCGAGGACACCGCCG-TGTACTACTGCGCCAGAAGCACCTACTACCGGCCC-CTGGACTACTGGGGCCAGGGCACCCTGGTGACCGT-GAGCAGC huCCR4 VH amino acid sequence: (SEQ ID NO: 2)
QVQLVQSGAEVKKPGASVKVSCKASGYT-
FASYYMHWMRQAPGQGLEWIGWINPG NVNT-
KYNEKFKGRATLTVDTSTNTAYMELSSL-
RSEDTAVYYCARSTYYRPLDYWG QGTLVTVSS huCCR4 $V_L$ nucleotide sequence: (SEQ ID NO: 3)
GACATCGTGATGACCCAGAGCCCCGA-
CAGCCTGGCCGTGAGCCTGGGC-
GAGCGGGCCACCAT CAACTGCAAGAGCAGCCA-
GAGCATCCTGTACAGCAGCAACCAGAAGAACTA
CCTGGCCTGGT ATCAGCAGAAGCCCGGCCAGAGC-
CCCAAGCTGCTGATCTACTGGGCCAG-
CACCCGGGAGAGC GGCGTGCCCGACCGGTT-
TAGCGGCAGCGGCTCCGGCACCGACTTCACCCT
GACCATCAGCAG CCTGCAGGCCGAGGACGTGGC-
CGTGTACTACTGCCACCAGTACCTGAG-
CAGCTACACCTTCG GCCAGGGCACAAAGCTG-
GAAATCAAG huCCR4 $V_L$ amino acid sequence: (SEQ ID NO: 4)
DIVMTQSPDSLAVSLGERATINCKSSQS-
ILYSSNQKNYLAWYQQKPGQSPKLLIYWA STRES-
GVPDRFSGSGSGTDFTLTISSLQAED-
VAVYYCHQYLSSYTFGQGTKLEIK In various embodiments, HCDR2 includes the amino acid sequence of WINXXNXNXKYNEKFKG (SEQ ID NO:11), HCDR3 includes the amino acid sequence of SXYXXPLDX (SEQ ID NO: 12), LCDR1 includes the amino acid sequence of KSSQSXLYSXXXXNYLA (SEQ ID NO: 13); LCDR2 includes the amino acid sequence of WASXXES (SEQ ID NO: 14); and LCDR3 includes the amino acid sequence of HQYLXXYT (SEQ ID NO: 15). As used herein X is meant to denote any natural, unnatural amino acid or amino acid analogue. For example, X is an alanine.

Antibodies

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically binds" or "immunoreacts with" is meant that the antibody reacts with one or more antigenic determinants of the desired antigen and does not react with other polypeptides. Antibodies include, but are not limited to, polyclonal, monoclonal, chimeric, dAb (domain antibody), single chain, $F_{ab}$, $F_{ab'}$ and $F_{(ab')2}$ fragments, scFvs, and $F_{ab}$ expression libraries.

A single chain Fv ("scFv") polypeptide molecule is a covalently linked $V_H::V_L$ heterodimer, which can be expressed from a gene fusion including $V_H$- and $V_L$-encoding genes linked by a peptide-encoding linker. (See Huston et al. (1988) Proc Nat Acad Sci USA 85(16):5879-5883). A number of methods have been described to discern chemical structures for converting the naturally aggregated, but chemically separated, light and heavy polypeptide chains from an antibody V region into an scFv molecule, which will fold into a three dimensional structure substantially similar to the structure of an antigen-binding site. See, e.g., U.S. Pat. Nos. 5,091,513; 5,132,405; and 4,946,778.

Very large naïve human scFv libraries have been and can be created to offer a large source of rearranged antibody genes against a plethora of target molecules. Smaller libraries can be constructed from individuals with infectious diseases in order to isolate disease-specific antibodies. (See Barbas et al., Proc. Natl. Acad. Sci. USA 89:9339-43 (1992); Zebedee et al., Proc. Natl. Acad. Sci. USA 89:3175-79 (1992)).

Figure 2:
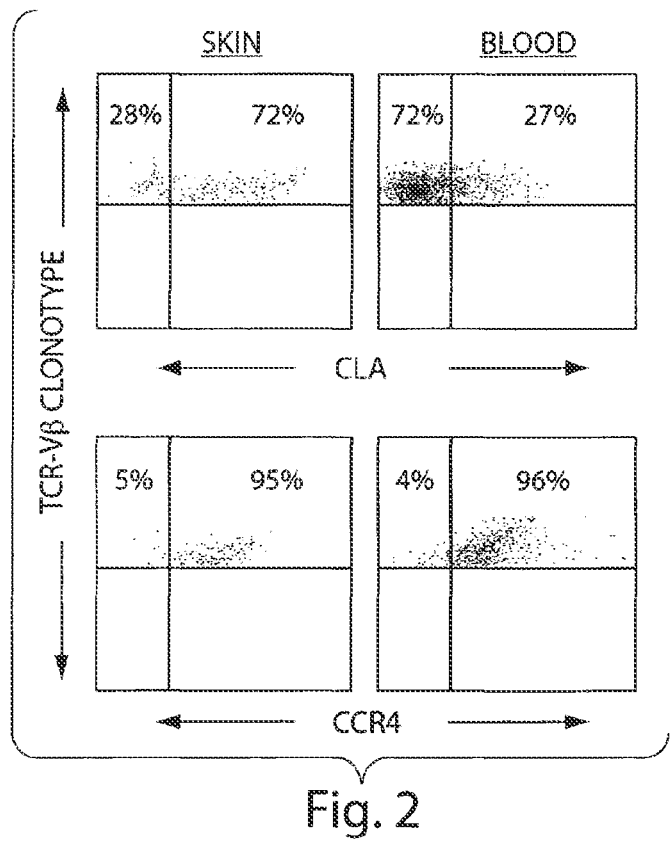
FIG. 2 are schematics showing FACS analysis of CTCL cells from leukemic CTCL patient and CTCL cells from skin lesion. The correlation between CLA loss (from 72% in skin to 27% in blood) and appearance of CTCL cells in the blood (demonstrated by the presence of CCR4+ cells in the blood) suggests the CLA loss itself may contribute to the evolution from localized CTCL lesions to full-blown leukemic CTCL.

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. The term "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." CDRs for the VH and VL regions of the scFv antibodies are shown in FIG. 2.

As used herein, the term "epitope" includes any protein determinant capable of specific binding to an immunoglobulin, an scFv, or a T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to a CCR4 epitope when the equilibrium binding constant ($K_d$) is ≤1 µM, preferably ≤100 nM, more preferably ≤10 nM, and most preferably ≤100 pM to about 1 pM, as measured by assays such as radioligand binding assays or similar assays known to those skilled in the art.

An CCR4 protein of the invention, or a derivative, fragment, analog, homolog or ortholog thereof, may be utilized as an immunogen in the generation of antibodies that immunospecifically bind these protein components.

Those skilled in the art will recognize that it is possible to determine, without undue experimentation, if a human monoclonal antibody has the same specificity as a human monoclonal antibody of the invention by ascertaining whether the former prevents the latter from binding to CCR4. If the human monoclonal antibody being tested competes with the human monoclonal antibody of the invention, as shown by a decrease in binding by the human monoclonal antibody of the invention, then it is likely that the two monoclonal antibodies bind to the same, or to a closely related, epitope.

Another way to determine whether a human monoclonal antibody has the specificity of a human monoclonal antibody of the invention is to pre-incubate the human monoclonal antibody of the invention with the CCR4 protein, with which it is normally reactive, and then add the human monoclonal antibody being tested to determine if the human monoclonal antibody being tested is inhibited in its ability to bind CCR4. If the human monoclonal antibody being tested is inhibited then, in all likelihood, it has the same, or functionally equivalent, epitopic specificity as the monoclonal antibody of the invention. Screening of human monoclonal antibodies of the invention, can be also carried out by utilizing CCR4 and determining whether the test monoclonal antibody is able to neutralize CCR4.

Various procedures known within the art may be used for the production of polyclonal or monoclonal antibodies directed against a protein of the invention, or against derivatives, fragments, analogs homologs or orthologs thereof (See, for example, Antibodies: A Laboratory Manual, Harlow E, and Lane D, 1988, Cold Spring Harbor Laboratory Press, Cold Spring Harbor, N.Y., incorporated herein by reference).

Antibodies can be purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

The term "monoclonal antibody" or "MAb" or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

Monoclonal antibodies can be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103) Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816, 567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Fully human antibodies are antibody molecules in which the entire sequence of both the light chain and the heavy chain, including the CDRs, arise from human genes. Such antibodies are termed "humanized antibodies", "human antibodies", or "fully human antibodies" herein. Human monoclonal antibodies can be prepared by using trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries. (See Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al., Bio/Technology 10, 779-783 (1992); Lonberg et al., Nature 368 856-859 (1994); Morrison, Nature 368, 812-13 (1994); Fishwild et al, Nature Biotechnology 14, 845-51 (1996); Neuberger, Nature Biotechnology 14, 826 (1996); and Lonberg and Huszar, Intern. Rev. Immunol. 13 65-93 (1995).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv (scFv) molecules.

An example of a method of producing a nonhuman host, exemplified as a mouse, lacking expression of an endogenous immunoglobulin heavy chain is disclosed in U.S. Pat. No. 5,939,598. It can be obtained by a method, which includes deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

One method for producing an antibody of interest, such as a human antibody, is disclosed in U.S. Pat. No. 5,916,771. This method includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

The antibody can be expressed by a vector containing a DNA segment encoding the single chain antibody described above.

These can include vectors, liposomes, naked DNA, adjuvant-assisted DNA, gene gun, catheters, etc. Vectors include chemical conjugates such as described in WO 93/64701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci USA 87:1149 (1990), Adenovirus Vectors (see LeGal LaSalle et al., Science, 259:988 (1993); Davidson, et al., Nat. Genet 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g. adenovirus, HSV) to a desired location. Additionally, the particles can be delivered by intracerebroventricular (icv) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266: 292-305 (1994)). Other methods that can be used include catheters, intravenous, parenteral, intraperitoneal and subcutaneous injection, and oral or other known routes of administration.

These vectors can be used to express large quantities of antibodies that can be used in a variety of ways. For example, to detect the presence of CCR4 in a sample. The antibody can also be used to try to bind to and disrupt a CCR4 activity.

Techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275-1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Heteroconjugate antibodies are also within the scope of the present invention. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody of the invention with respect to effector function, so as to enhance, e.g., the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies or to other molecules of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun 133:1335-2549 (1984); Jansen et al., Immunological Reviews 62:185-216 (1982); and Vitetta et al., Science 238: 1098 (1987)). Preferred linkers are described in the literature. (See, for example, Ramakrishnan, S. et al., Cancer Res.

44:201-208 (1984) describing use of MBS (M-maleimido-benzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6[3-(2-pyridyldithio)-propianamide]hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

Use of Antibodies Against CCR4

Methods for the screening of antibodies that possess the desired specificity include, but are not limited to, enzyme linked immunosorbent assay (ELISA) and other immunologically mediated techniques known within the art.

Antibodies directed against a CCR4 protein (or a fragment thereof) may be used in methods known within the art relating to the localization and/or quantitation of a CCR4 protein (e.g., for use in measuring levels of the CCR4 protein within appropriate physiological samples, for use in diagnostic methods, for use in imaging the protein, and the like). In a given embodiment, antibodies specific to a CCR4 protein, or derivative, fragment, analog or homolog thereof, that contain the antibody derived antigen binding domain, are utilized as pharmacologically active compounds (referred to hereinafter as "Therapeutics").

An antibody specific for a CCR4 protein of the invention can be used to isolate a CCR4 polypeptide by standard techniques, such as immunoaffinity, chromatography or immunoprecipitation. Antibodies directed against a CCR4 protein (or a fragment thereof) can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibodies of the invention, including polyclonal, monoclonal, humanized and fully human antibodies, may used as therapeutic agents. Such agents will generally be employed to treat or prevent cancer in a subject, increase vaccine efficiency or augment a natural immune response. An antibody preparation, preferably one having high specificity and high affinity for its target antigen, is administered to the subject and will generally have an effect due to its binding with the target. Administration of the antibody may abrogate or inhibit or interfere with an activity of the CCR4 protein.

A therapeutically effective amount of an antibody of the invention relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Antibodies specifically binding a CCR4 protein or a fragment thereof of the invention, as well as other molecules identified by the screening assays disclosed herein, can be administered for the treatment of cancer or other proliferative disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa., 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods.

An antibody according to the invention can be used as an agent for detecting the presence of CCR4 (or a protein or a protein fragment thereof) in a sample. Preferably, the antibody contains a detectable label. Antibodies can be polyclonal, or more preferably, monoclonal. An intact antibody, or a fragment thereof (e.g., $F_{ab}$, scFv, or $F_{(ab)2}$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N. J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Pharmaceutical Compositions

The antibodies or agents of the invention (also referred to herein as "active compounds"), and derivatives, fragments, analogs and homologs thereof, can be incorporated into pharmaceutical compositions suitable for administration. Such compositions typically comprise the antibody or agent and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Screening Methods

The invention provides methods (also referred to herein as "screening assays") for identifying modulators, i.e., candidate or test compounds or agents (e.g., peptides, peptidomimetics, small molecules or other drugs) that modulate or otherwise interfere with an CCR4 activity. Also provided are methods of identifying compounds useful to treat cancer. The invention also encompasses compounds identified using the screening assays described herein.

For example, the invention provides assays for screening candidate or test compounds which modulate the CCR4 carbonic anhydrase activity. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. (See, e.g., Lam, 1997. Anticancer Drug Design 12: 145).

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. Proc. Natl. Acad. Sci. U.S.A. 90: 6909; Erb, et al., 1994. Proc. Natl. Acad. Sci. U.S.A. 91: 11422; Zuckermann, et al., 1994. J. Med. Chem. 37: 2678; Cho, et al., 1993. Science 261: 1303;

Carrell, et al., 1994. Angew. Chem. Int. Ed. Engl. 33: 2059; Carell, et al., 1994. Angew. Chem. Int. Ed. Engl. 33: 2061; and Gallop, et al., 1994. J. Med. Chem. 37: 1233.

Libraries of compounds may be presented in solution (see e.g., Houghten, 1992. Biotechniques 13: 412-421), or on beads (see Lam, 1991. Nature 354: 82-84), on chips (see Fodor, 1993. Nature 364: 555-556), bacteria (see U.S. Pat. No. 5,223,409), spores (see U.S. Pat. No. 5,233,409), plasmids (see Cull, et al., 1992. Proc. Natl. Acad. Sci. USA 89: 1865-1869) or on phage (see Scott and Smith, 1990. Science 249: 386-390; Devlin, 1990. Science 249: 404-406; Cwirla, et al., 1990. Proc. Natl. Acad. Sci. U.S.A. 87: 6378-6382; Felici, 1991. J. Mol. Biol. 222: 301-310; and U.S. Pat. No. 5,233, 409.).

In one embodiment, a candidate compound is introduced to an antibody-antigen complex and determining whether the candidate compound disrupts the antibody-antigen complex, wherein a disruption of this complex indicates that the candidate compound modulates an CCR4 activity.

In another embodiment, at least one CCR4 protein is provided, which is exposed to at least one neutralizing monoclonal antibody. Formation of an antibody-antigen complex is detected, and one or more candidate compounds are introduced to the complex. If the antibody-antigen complex is disrupted following introduction of the one or more candidate compounds, the candidate compounds is useful to treat cancer or a proliferative disease or disorder, particularly a renal proliferative disorder.

Determining the ability of the test compound to interfere with or disrupt the antibody-antigen complex can be accomplished, for example, by coupling the test compound with a radioisotope or enzymatic label such that binding of the test compound to the antigen or biologically-active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product.

In one embodiment, the assay comprises contacting an antibody-antigen complex with a test compound, and determining the ability of the test compound to interact with the antigen or otherwise disrupt the existing antibody-antigen complex. In this embodiment, determining the ability of the test compound to interact with the antigen and/or disrupt the antibody-antigen complex comprises determining the ability of the test compound to preferentially bind to the antigen or a biologically-active portion thereof, as compared to the antibody.

In another embodiment, the assay comprises contacting an antibody-antigen complex with a test compound and determining the ability of the test compound to modulate the antibody-antigen complex. Determining the ability of the test compound to modulate the antibody-antigen complex can be accomplished, for example, by determining the ability of the antigen to bind to or interact with the antibody, in the presence of the test compound.

Those skilled in the art will recognize that, in any of the screening methods disclosed herein, the antibody may be a CCR4 neutralizing antibody. Additionally, the antigen may be a CCR4 protein, or a portion thereof (e.g., the CA domain).

The screening methods disclosed herein may be performed as a cell-based assay or as a cell-free assay. In the case of cell-free assays comprising the membrane-bound forms of the CCR4 proteins, it may be desirable to utilize a solubilizing agent such that the membrane-bound form of the proteins are maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, N-dodecyl-N,N-dimethyl-3-ammonio-1-propane sulfonate, 3-(3-cholamidopropyl)dimethylamminiol-1-propane sulfonate (CHAPS), or 3-(3-cholamidopropyl)dimethylamminiol-2-hydroxy-1-propane sulfonate (CHAPSO).

In more than one embodiment, it may be desirable to immobilize either the antibody or the antigen to facilitate separation of complexed from uncomplexed forms of one or both following introduction of the candidate compound, as well as to accommodate automation of the assay. Observation of the antibody-antigen complex in the presence and absence of a candidate compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, GST-antibody fusion proteins or GST-antigen fusion proteins can be adsorbed onto glutathione sepharose beads (Sigma Chemical, St. Louis, Mo.) or glutathione derivatized microtiter plates, that are then combined with the test compound, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly. Alternatively, the complexes can be dissociated from the matrix, and the level of antibody-antigen complex formation can be determined using standard techniques.

Other techniques for immobilizing proteins on matrices can also be used in the screening assays of the invention. For example, either the antibody or the antigen (e.g. the CCR4 protein or the CA domain thereof) can be immobilized utilizing conjugation of biotin and streptavidin. Biotinylated antibody or antigen molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, other antibodies reactive with the antibody or antigen of interest, but which do not interfere with the formation of the antibody-antigen complex of interest, can be derivatized to the wells of the plate, and unbound antibody or antigen trapped in the wells by antibody conjugation. Methods for detecting such complexes, in addition to those described above for the GST-immobilized complexes, include immunodetection of complexes using such other antibodies reactive with the antibody or antigen.

The invention further pertains to novel agents identified by any of the aforementioned screening assays and uses thereof for treatments as described herein.

Diagnostic Assays

Antibodies of the present invention can be detected by appropriate assays, e.g., conventional types of immunoassays. For example, a sandwich assay can be performed in which a CCR4 protein or fragment thereof (e.g., the CA domain) is affixed to a solid phase. Incubation is maintained for a sufficient period of time to allow the antibody in the sample to bind to the immobilized polypeptide on the solid phase. After this first incubation, the solid phase is separated from the sample. The solid phase is washed to remove unbound materials and interfering substances such as non-specific proteins which may also be present in the sample. The solid phase containing the antibody of interest bound to the immobilized polypeptide is subsequently incubated with a second, labeled antibody or antibody bound to a coupling agent such as biotin or avidin. This second antibody may be another anti-CCR4 antibody or another antibody. Labels for antibodies are well-known in the art and include radionuclides, enzymes (e.g. maleate dehydrogenase, horseradish peroxidase, glucose oxidase, catalase), fluors (fluorescein isothiocyanate, rhodamine, phycocyanin, fluorescarmine), biotin, and the like. The labeled antibodies are incubated with the solid and the label bound to the solid phase is measured. These and other immunoassays can be easily performed by those of ordinary skill in the art.

The anti-CCR4 antibodies and scFv antibodies of the invention, when joined to a detectable moiety, provides a way for detecting "cancerous tissue" or tissue subject to aberrant cell proliferation and therefore at risk for cancer. In addition to tissue that becomes cancerous due to an in situ neoplasm, for example, the antibody-detectable moiety conjugates also provides a method of detecting cancerous metastatic tissue present in distal organs and/or tissues. Thus such tissue may be detected by contacting tissue suspected of being cancerous with the antibody-detectable moiety under appropriate conditions to cause the detectable moiety to be detected in cancerous tissue, thereby detecting the presence of cancerous tissue.

The detectable moieties can be conjugated directly to the antibodies or fragments, or indirectly by using, for example, a fluorescent secondary antibody. Direct conjugation can be accomplished by standard chemical coupling of, for example, a fluorophore to the antibody or antibody fragment, or through genetic engineering. Chimeras, or fusion proteins can be constructed which contain an antibody or antibody fragment coupled to a fluorescent or bioluminescent protein. For example, Casadei, et al., describe a method of making a vector construct capable of expressing a fusion protein of aequorin and an antibody gene in mammalian cells.

As used herein, the term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject (such as a biopsy), as well as tissues, cells and fluids present within a subject. That is, the detection method of the invention can be used to detect cancer, a cancer cell, or a cancer-associated cell (such as a stromal cell associated with a tumor or cancer cell) in a biological sample in vitro as well as in vivo. For example, in vitro techniques for detection of CCR4 include enzyme linked immunosorbent assays (ELISAs), Western blots, immunoprecipitations, and immunofluorescence. Furthermore, in vivo techniques for detection of CCR4 include introducing into a subject a labeled anti-CCR4 antibody. For example, the antibody can be labeled with a radioactive marker whose presence and location in a subject can be detected by standard imaging techniques. In embodiments, the invention provides a non-invasive method of detecting a tumor or cancer cell in a subject. The subject is administered an antibody or scFv antibody of the invention, where the antibody is linked to a detectable moiety (i.e., any moiety capable of being detected by, e.g., fluorescent, chemical, chemiluminescent, radioactive, or other means known in the art), the antibody is allowed to localize to the tumor then is detected by observation of the detectable moiety.

In the case of "targeted" conjugates, that is, conjugates which contain a targeting moiety—a molecule or feature designed to localize the conjugate within a subject or animal at a particular site or sites, localization refers to a state when an equilibrium between bound, "localized", and unbound, "free" entities within a subject has been essentially achieved. The rate at which such an equilibrium is achieved depends upon the route of administration. For example, a conjugate administered by intravenous injection to localize thrombi may achieve localization, or accumulation at the thrombi, within minutes of injection. On the other hand, a conjugate administered orally to localize an infection in the intestine may take hours to achieve localization. Alternatively, localization may simply refer to the location of the entity within the subject or animal at selected time periods after the entity is administered. By way of another example, localization is achieved when an moiety becomes distributed following administration.

In all of the above cases, a reasonable estimate of the time to achieve localization may be made by one skilled in the art. Furthermore, the state of localization as a function of time may be followed by imaging the detectable moiety (e.g., a light-emitting conjugate) according to the methods of the invention, such as with a photodetector device. The "photodetector device" used should have a high enough sensitivity to enable the imaging of faint light from within a mammal in a reasonable amount of time, and to use the signal from such a device to construct an image.

In cases where it is possible to use light-generating moieties which are extremely bright, and/or to detect light-generating fusion proteins localized near the surface of the subject or animal being imaged, a pair of "night-vision" goggles or a standard high-sensitivity video camera, such as a Silicon Intensified Tube (SIT) camera (e.g., from Hammamatsu Photonic Systems, Bridgewater, N.J.), may be used. More typically, however, a more sensitive method of light detection is required.

In extremely low light levels the photon flux per unit area becomes so low that the scene being imaged no longer appears continuous. Instead, it is represented by individual photons which are both temporally and spatially distinct form one another. Viewed on a monitor, such an image appears as scintillating points of light, each representing a single detected photon. By accumulating these detected photons in a digital image processor over time, an image can be acquired and constructed. In contrast to conventional cameras where the signal at each image point is assigned an intensity value, in photon counting imaging the amplitude of the signal carries no significance. The objective is to simply detect the presence of a signal (photon) and to count the occurrence of the signal with respect to its position over time.

At least two types of photodetector devices, described below, can detect individual photons and generate a signal which can be analyzed by an image processor. Reduced-Noise Photodetection devices achieve sensitivity by reducing the background noise in the photon detector, as opposed to amplifying the photon signal. Noise is reduced primarily by cooling the detector array. The devices include charge coupled device (CCD) cameras referred to as "backthinned", cooled CCD cameras. In the more sensitive instruments, the cooling is achieved using, for example, liquid nitrogen, which brings the temperature of the CCD array to approximately −120° C. "Backthinned" refers to an ultra-thin backplate that reduces the path length that a photon follows to be detected, thereby increasing the quantum efficiency. A particularly sensitive backthinned cryogenic CCD camera is the "TECH 512", a series 200 camera available from Photometrics, Ltd. (Tucson, Ariz.).

"Photon amplification devices" amplify photons before they hit the detection screen. This class includes CCD cameras with intensifiers, such as microchannel intensifiers. A microchannel intensifier typically contains a metal array of channels perpendicular to and co-extensive with the detection screen of the camera. The microchannel array is placed between the sample, subject, or animal to be imaged, and the camera. Most of the photons entering the channels of the array contact a side of a channel before exiting. A voltage applied across the array results in the release of many electrons from each photon collision. The electrons from such a collision exit their channel of origin in a "shotgun" pattern, and are detected by the camera.

Even greater sensitivity can be achieved by placing intensifying microchannel arrays in series, so that electrons generated in the first stage in turn result in an amplified signal of electrons at the second stage. Increases in sensitivity, however, are achieved at the expense of spatial resolution, which decreases with each additional stage of amplification. An exemplary microchannel intensifier-based single-photon detection device is the C2400 series, available from Hamamatsu.

Image processors process signals generated by photodetector devices which count photons in order to construct an image which can be, for example, displayed on a monitor or printed on a video printer. Such image processors are typically sold as part of systems which include the sensitive photon-counting cameras described above, and accordingly, are available from the same sources. The image processors are usually connected to a personal computer, such as an IBM-compatible PC or an Apple Macintosh (Apple Computer, Cupertino, Calif.), which may or may not be included as part of a purchased imaging system. Once the images are in the form of digital files, they can be manipulated by a variety of image processing programs (such as "ADOBE PHOTOSHOP", Adobe Systems, Adobe Systems, Mt. View, Calif.) and printed.

In one embodiment, the biological sample contains protein molecules from the test subject. One preferred biological sample is a peripheral blood leukocyte sample isolated by conventional means from a subject.

The invention also encompasses kits for detecting the presence of CCR4 or a CCR4-expressing cell in a biological sample. For example, the kit can comprise: a labeled compound or agent capable of detecting a cancer or tumor cell (e.g., an anti-CCR4 scFv or monoclonal antibody) in a biological sample; means for determining the amount of CCR4 in the sample; and means for comparing the amount of CCR4 in the sample with a standard. The standard is, in some embodiments, a non-cancer cell or cell extract thereof. The compound or agent can be packaged in a suitable container. The kit can further comprise instructions for using the kit to detect cancer in a sample.

Methods of Treatment

The invention provides for both prophylactic and therapeutic methods of treating a subject at risk of (or susceptible to) a cancer, or other cell proliferation-related diseases or disorders. Such diseases or disorders include but are not limited to, e.g., those diseases or disorders associated with aberrant expression of CCR4. For example, the methods are used to treat, prevent or alleviate a symptom of a hematologic cancer such cutaneous T-cell Lymphoma (CTCL), mycosis fungoides (MF), primary cutaneous anaplastic large cell Lymphoma (cutaneous ALCL), Sezary syndrome, or adult T cell Leukemia/Lymphoma (ATLL). Alternatively, the methods are used to treat, prevent or alleviate a symptom of a solid tumor such as s breast cancer, lung cancer, ovarian cancer, prostate cancer, colon cancer, cervical cancer, brain cancer, liver cancer, pancreatic cancer or stomach cancer.

Accordingly, one aspect, the invention provides methods for preventing, treating or alleviating a symptom cancer or a cell proliferative disease or disorder in a subject by administering to the subject a monoclonal antibody or scFv antibody of the invention. For example, a huCCR4 antibody may be administered in therapeutically effective amounts.

Subjects at risk for cancer or cell proliferation-related diseases or disorders include patients who have a family history of cancer or a subject exposed to a known or suspected cancer-causing agent. Administration of a prophylactic agent can occur prior to the manifestation of cancer such that the disease is prevented or, alternatively, delayed in its progression.

In another aspect, tumor cell growth is inhibited or suppressor T-cell activity is decreased by contacting a cell with an CCR4 antibody of the invention. The cell is any cell that express CCR4. For example the cell is T-cell.

Also included in the invention are methods of increasing or enhancing an immune response to an antigen. An immune response is increased or enhanced by administering to the subject a monoclonal antibody or scFv antibody of the invention. The antigen is a viral (e.g. HIV), bacterial, fungal or tumor antigen. The immune response is a natural immune response. By natural immune response is meant an immune response that is a result of an infection. The infection is a chronic infection.

Alternatively, the immune response is a response induced due to a vaccination. Accordingly, in another aspect the invention provides a method of increasing vaccine efficiency by administering to the subject a monoclonal antibody or scFv antibody of the invention and a vaccine. The antibody and the vaccine are administered sequentially or concurrently. The vaccine is a tumor vaccine a bacterial vaccine or a viral vaccine.

The immune response is augmented for example by augmenting antigen specific T effector function.

Combinatory Methods

The invention provides treating cancer in a patient by administering two antibodies that bind to the same epitope of the CCR4 protein or, alternatively, two different epitopes of the CCR4 protein. Also, the cancer is treated by administering a first antibody that binds to CCR4 and a second antibody that binds to a protein other than CCR4.

Additionally, the invention provides administration of an antibody that binds to the CCR4 protein and an anti-neoplastic agent, such a small molecule, a growth factor, a cytokine or other therapeutics including biomolecules such as peptides, peptidomimetics, peptoids, polynucleotides, lipid-derived mediators, small biogenic amines, hormones, neuropeptides, and proteases. Small molecules include, but are not limited to, inorganic molecules and small organic molecules. Suitable growth factors or cytokines include an IL-2, GM-CSF, IL-12, and TNF-alpha. Small molecule libraries are known in the art. (See, Lam, Anticancer Drug Des., 12:145, 1997.)

The invention will be further described in the following examples, which do not limit the scope of the invention described in the claims.

EXAMPLES

Example 1

General Methods

Acquisition, Characterization, and Quantification of CCR4-Bearing Cell Types.

Fresh, high-quality buffy-coats of human white bloods cells are received daily from the Blood Banks at Children's Hospital, Dana-Farber Cancer Center and Brigham and Women's Hospital. Upon receiving these samples, white blood cell populations are fractionated into granulocyte and PBMC subunits using Ficoll gradients.

Reagents are also tested on peripheral blood from leukemic CTCL patients, as a "reality check" to ensure that experimental data, with respect to normal CCR4-bearing populations, is applicable to true target populations. Such samples are available by informed consent from leukemic CTCL patients. PBMC is prepared as follows. Human granulocyte or PBMC is incubated on ice with Mab1567 for 45 minutes. Equal numbers of cells are treated in parallel with control human IgG1 Mabs or with PBS. "Charged" Dynabeads are added to the MAb-bound cells and incubated with gentle rotation. Following this incubation, Mab-bound and non-bound populations are magnetically separated. These steps generate 3 cell populations: 1) cells depleted via a "mock" antibody (PBS); 2) cells depleted via a "negative control" or "irrelevant" Mab; and 3) cells depleted via Mab 1567. The three types of cell populations are extensively immunophenotyped for comparison with each other using at least 10 different fluorescent antibody cocktails.

The relative proportions of various lymphocyte populations among the 3 different cell populations are immunophenotyped, by using a 6-color Cytomation cytometer and an extensive repertoire of fluorescently-labeled Mabs, more than 50 non-overlapping subsets of lymphocytes within human peripheral blood are distinguished (Campbell J. J. et al. Nature 1999, 400:776-780; Campbell J. J. et al. J Immunol 2001, 166:877-884; Soler D. et al. Blood 2003, 101:1677-1682; Kunkel E. J. et al. Am J Pathol 2002, 160:347-355; Campbell J. J. et al. J Cell Biol 1998, 141:1053-1059). Memory, effector and naïve CD4 T cell subsets; memory, effector and naïve CD8 T cell subsets; memory and naïve B cells subsets; NK subsets; NKT subsets; Treg; and dendritic cell subsets are identified and quantified using this method. In the granulocyte populations, the relative proportions of eosinophils, basophils and neutrophils are quantified.

Quantification of CCR4 Expression Levels.

FACS analysis is used to determine the number of CCR4 molecules on the surface of $CD4^+/CCR4^+$ T cells by comparing relative levels of FACS binding of the Mab 1567 at under physiological and saturated conditions. Cells from different healthy individuals are examined to evaluate heterogeneity of expression patterns in the population, as well as from the blood of patients with Sezary syndrome, and other CTCLs. A Mann-Whitney U test is used to determine if any significant differences exist between CCR4 level of expression across various cell types. The simultaneous analysis of multiple markers from the same donor allows for a paired t-test with a two-tailed distribution analysis to be applied to the analysis of $CD4^+$ T cell subsets.

Immunohistochemical Analyses

Frozen CTCL tissue blocks are retrieved from the SPORE Biospecimen Access and Analysis Core. Frozen tissue is also obtained from normal skin samples from plastic surgery cases. Following fixation, sequential sections are incubated with Mab1567 (Mab 1G1 serves as a positive control), washed, and then incubated with horseradish peroxidase (HRP)-labeled anti-human IgG1 Mab. Antibody localization will be visualized using a peroxidase reaction using diaminobenzidine (DAB) as a chromogen (Dako). Slides are counterstained with methylene green, dehydrated, and mounted with Polymount (Polysciences). A control slide substituting an irrelevant human IgG1 Mab for Mab 1567 is included in all cases.

Example 2

Distinguishing CTCL Clones and Normal T Cells in Leukemic CTCL Blood

Immunophenotypic diversity observed within CTCL blood samples results from the presence of persisting "normal" CD4 T cells in the midst of the transformed CTCL cells. To identify leukemic CTCL clonally-expanded populations amongst the healthy cells, a systematic method of characterization of leukemic cells was developed based on differential expression of unique T cell receptors (TCRs). Individual T cell clones each express a unique TCR heterodimer consisting of an α-chain and a β-chain. Each β-chain is derived from random recombination of "V", "D" and "J" segments within the TCR locus of the T cell genome during development (Abbas A, Lichtman, A H. Cellular And Molecular Immunology, Updated Edition (ed 5). Elsevier Saunders 2005). There are only a limited number of TCR-Vβ genes available for recombination. The "V" portion of TCRs on the surface of an individual T cell can be recognized by monoclonal antibodies via flow cytometry. Such antibodies are commercially available for a large proportion of the known TCR-Vβs. Approximately half of the leukemic CTCL patients who were tested possessed a grossly overrepresented population of CD4 T cells bearing a single TCR-Vβ. These expanded populations (never seen in normal donors) correspond to the clonally-derived, transformed CTCL component of the CD4 pool. Expanded populations that express TCR-Vβ segments not covered by the antibody panel likely account for the leukemic CTCL patients without an identifiable clone. Once an expanded CD4 T clone from a particular leukemic CTCL patient was identified, the resulting unique profile was used to discriminate CTCL cells from the remaining "normal" CD4 T cells for that particular patient. Multi-color flow cytometry was then used to sequester cells displaying this unique profile as well as extensively analyze the phenotype of these pure CTCL cells.

Example 3

CCR4 is a Marker for CTCL Clones

Our analysis of CTCL clones was primarily borne from the hypothesis that CTCL cells are transformed versions of normal skin-homing memory CD4 T cells. Cutaneous CD4 lymphocytes from normal human blood have been identified by their co-expression of the cutaneous lymphocyte antigen (CLA) (Campbell J. J. et al. J Cell Biol 1998, 141:1053-1059) and the chemokine receptor CCR4 (Campbell J. J. et al. Nature 1999, 400:776-780; Kunkel E. J. et al. Am J Pathol 2002, 160:347-355). In addition, the chemokine receptor CCR10 is expressed exclusively by a subset of cutaneous CD4 T cells (Soler D. et al. Blood 2003, 101:1677-1682). The expression of CLA, CCR4 and CCR10, identified by clonal expression of unique TCR-Vβ segments, on CTCL cells was analyzed (FIG. 1). CTCL cells expressed each of these markers to varying degrees. This finding can be explained by each of the following two hypotheses: 1) CTCL cells have derived from a non-cutaneous CD4 population that has usurped the cutaneous homing markers expressed by normal skin T cells; or 2) CTCL cells are transformed cells derived from normal cutaneous-homing T cells. To distinguish between these two potential sources of CLA+/CCR4+/CCR10+ clones, CTCL cells purified from skin lesions and peripheral blood sampled from leukemic CTCL patients were examined (FIG. 2). The results showed that CCR4 was expressed by essentially all CTCL cells from both sources. Most of the CTCL cells from the skin lesions expressed CLA, in marked contrast to CTCL cells from blood, which expressed significantly reduced levels of CLA. This finding suggested that loss of CLA expression correlated with increasing numbers of CTCL cells in patient blood. Because CLA is an adhesion molecule necessary for the homing of cutaneous T cells to the skin it is reasonable to posit that loss of CLA expression (and therefore exclusion from the skin) plays an important role in the extracutaneous spread (e.g., blood, lymph nodes, viscera) of more aggressive variants of CTCL. However, some forms of CTCL emerge and spread by a different pattern. CTCL of the mycosis fungoides variant is often an indolent lymphoma, with transformed cells occurring only rarely in the blood (Yawalkar N. et al. Blood 2003, 102:4059-4066; Robert C, Kupper T S. N Engl J Med 1999, 341:1817-1828). In some cases, the disease advances into leukemic CTCL, with large numbers of cells appearing in the blood. In other cases, CTCL first presents as a leukemic disease involving both blood and skin.

Data from previous studies have shown that CCL17 and CCL21 (both ligands for CCR4) are strongly expressed in lesional skin of CTCL patients (Ferenczi K. et al. J Invest Dermatol 2002, 119:1405-1410), facilitating the entry of and maintenance within skin of these malignant cells. However, without CLA to initiate the tethering of CTCL cells to cutaneous post-capillary venules, CCR4 cannot be engaged by its ligands within skin and the CTCL cells remain in the blood.

Example 4

Validation of CCR4 Flow Cytometry Studies

Figure 3:
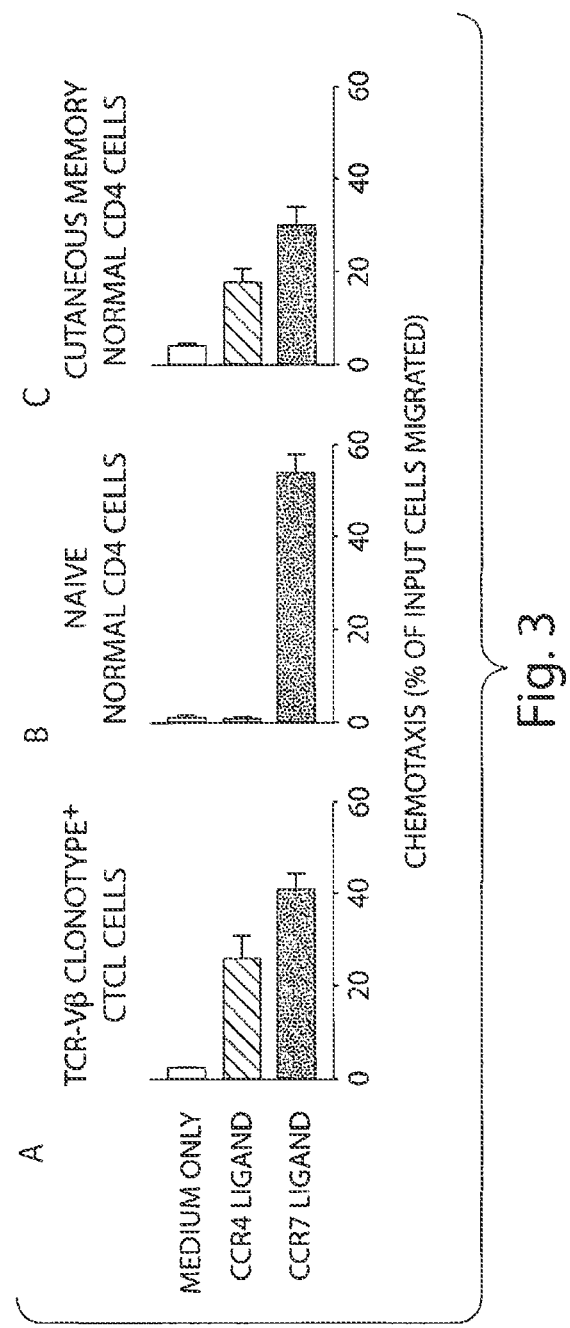
FIG. 3 are bar charts showing CTCL Cell Migratory Response Recapitulates That of Normal Cutaneous T Cells but Not Normal Naïve T Cells. In vitro chemotaxis assays demonstrate that CTCL cells display chemotactic migration in response to the CCR4 ligand CCL22 and the CCR7 ligand CCL21 (see panel A). Cutaneous memory cells display a similar pattern (see panel C), whereas naïve CD4 cells respond only to CCR7 ligand (see panel B). Data is mean±SD, 3 separate experiments, each experiment performed in duplicate.

Before embarking on a project to target CTCL via CCR4, it was necessary to validate that the staining patterns in FIGS. 1-2 accurately represent CCR4 expression by CTCL cells. Fortunately, because CCR4 is a chemotactic receptor, CCR4 function can be readily assessed by well-established in vitro migration assays. Peripheral blood was obtained from 3 different leukemic CTCL patients bearing a previously-identified TCR-Vβ clonal expansion. For each CTCL patient, peripheral blood mononuclear cells (PBMCs) from a normal donor were assessed in parallel as a positive control. Migratory ability was measured via the widely-used in vitro transwell chemotaxis assay (Kunkel E. J. et al. Am J Pathol 2002, 160:347-355; Campbell J. J. et al. J Cell Biol 1996, 134:255-266; Warnock R. A. et al. J Exp Med 2000, 191:77-88) (FIG. 3).

Cells were placed in an optimized gradient of a CCR4 ligand, a CCR7 ligand, or in the absence of chemokine. CTCL cells were stained for flow cytometry with CD4 and the appropriate anti-TCRVβ. Normal PBMCs were stained with CD4, CLA and CD45RA to identify naïve CD4 cells (CD4+/CD45RA$^{high}$) and cutaneous memory CD4 cells (CD4+/CD45RA$^{lo/neg}$/CLA+). All 3 cell types responded well to CCR7 ligand, but naïve cells responded best to this chemokine. Naïve CD4 cells did not respond detectably to CCR4 ligand. Both CTCL cells and normal cutaneous memory cells responded well to CCR4 ligand and, indeed, CTCL cells responded better. Thus, this independent functional assay proves that CTCL cells are responsive to CCR4 ligand.

Figure 4:
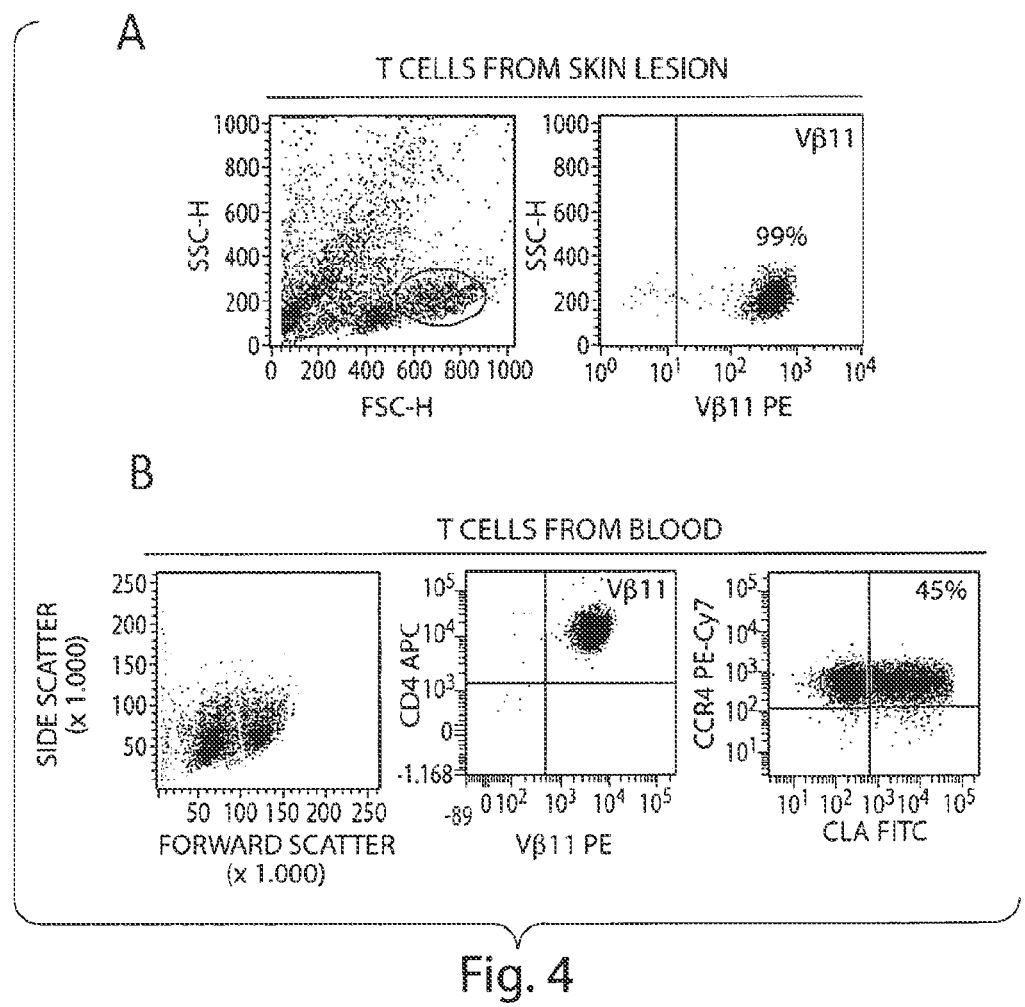
FIG. 4 are schematics showing FACS analysis of T cells isolated from the skin lesions (see panel A) and blood (see panel B) of a patient with stage IV CTCL. A unique high scatter population of T cells was present in both skin and blood; these cells represent a clonal population of malignant T cells. Malignant T cells from skin expressed both CLA and CCR4 (not shown) and malignant cells from blood expressed CCR4, but CLA expression varied.

T cells were also isolated from skin lesions of CTCL patients using short term explant cultures (Clark R. A. et al. J Invest Dermatol 2006, 126:1059-1070). Following analysis by flow cytometry, it was determined that CTCL skin lesions from all stages of disease contained a unique population of T cells with higher forward and side scatter. These high-scatter T cells were not seen in either normal skin or skin lesions of psoriasis, or in contact dermatitis or atopic dermatitis, suggesting that they do not represent antigen-activated T cells. The high-scatter T cell population was also evident in the blood of later-staged CTCL with known blood involvement but was absent in earlier stages of the disease. In late-stage patients, where malignant T cells were identified by their particular TCR Vβ expression, the high scatter T cell population from both skin and blood was clonal and malignant (FIG. 4). All malignant T cells from both blood and skin expressed CCR4, whereas the expression of CLA within skin-derived cells was more variable. This ability to discriminate malignant from benign T cells in early CTCL lesions enables more detailed study of the malignant T cells in this disorder and their selective depletion by Mab1567 based immunotherapy.

Example 5

ALCL Lines as In Vitro and In Vivo Models of CTCL Cells

It is well-established that CTCL cells are difficult to perpetuate in culture or grow in immunodeficient mice. To circumvent this obstacle, several human skin-tropic ALCL cell lines that are robust in culture and in animal models are used (Kleinhans M et. al. Blood 2003, 101:1487-1493; Li S. et al. Am J Pathol 2001, 158:1231-1237; Pfeifer W. et al. Am J Pathol 1999, 155:1353-1359; Zhang Q. et al. Proc Natl Acad Sci USA 1996, 93:9148-9153). Moreover, these cells form subcutaneous tumors when injected into immunodeficient mice (Pfeifer W. et al. Am J Pathol 1999, 155:1353-1359). Thus, these cells, called Mac-1 and Mac-2b, were immunophenotyped to determine if their expression profile of skin-related chemokine receptors is comparable to that of CTCL cells. The results showed that like CTCL cells, these ALCL lines expressed high levels of CCR4, CCR7 and CXCR4. These cell lines did not express significant levels of any of the other known chemokine receptors, including, for example, CCR5. The Mac-1/2b cell lines serve as particularly good models of CTCL because they are of human origin, express high levels of CCR4, and grow in immunodeficient mice. The ability of CCR4 Mabs to clear CCR4+ cells from a living animal is directly tested using an animal model of CTCL, created by injection of the Mac-1/2b cell line into immunodeficient mice. Because this model employs a cell line derived from human tissue, this method of Mab validation is superior to any other method using mouse cells. The results of these studies directly translate to human therapeutic strategies.

Example 6

In Vivo Immunodepletion of CCR4-Expressing Human Skin-Tropic ALCL Tumor Cells by Mab1567

Figure 5:
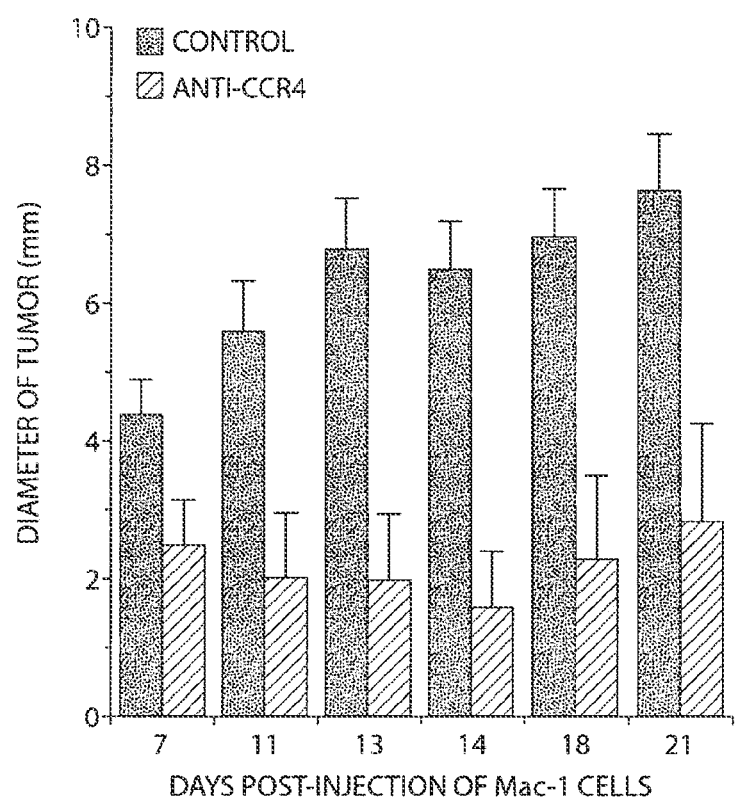
FIG. 5 is a bar chart showing Anti-Tumor Effect of Anti-CCR4 Mab 1567 in a CCR4$^+$ Human ALCL Tumor Xenograft Model. Mab treatment was initiated on day zero (d0) by i.p injection of 3 mg/kg Mab and continued 2 times per week for 5 weeks. Tumor size and growth were estimated by weekly measurement of tumor length and width by caliper photography. Results show that from seven days post-injection of Mac-1 cells and onward, control tumors continued to grow while mice treated with Mab1567 experienced reduced and arrested tumor growth. In mice receiving the Mab1567 antibody, a tumor formed, but the size of that tumor remained constant over the next two weeks through post-injection day 21.

The IgG2b murine Mab1567 and control murine Mab (1D4) were used to establish an immunotherapy model in severe combined immunodeficiency (SCID)/beige mice. There were 6 mice in each treatment group. Each animal received an intradermal (i.d.) injection of 1×10⁷ Mac-1 cells on one flank, followed immediately by intraperitoneal (i.p.) injection of 3 mg Mab, followed by bi-weekly Mab injections. As shown in FIG. 5, there was a marked inhibition of tumor cell growth. This is quite remarkable considering that these mice have no NK activity or ADCC, and that the antibody isotype IgG2b binds more avidly to immunoinhibitory FcγIII receptors than to immunoactivating FcγIII receptors (Nimmerjahn F, Ravetch J V. Science 2005, 310:1510-1512). Studies performed with a different chimeric mouse Mab showed that in vivo anti-tumor activity could be mediated indirectly by enhancement of phagocytic activity mediated by monocytes/macrophages (Ishida T, Ueda R. Cancer Sci 2006, 97:1139-1146).

Example 7

Cloning of the Mouse Anti-CCR4 Mab1567

Figure 6:
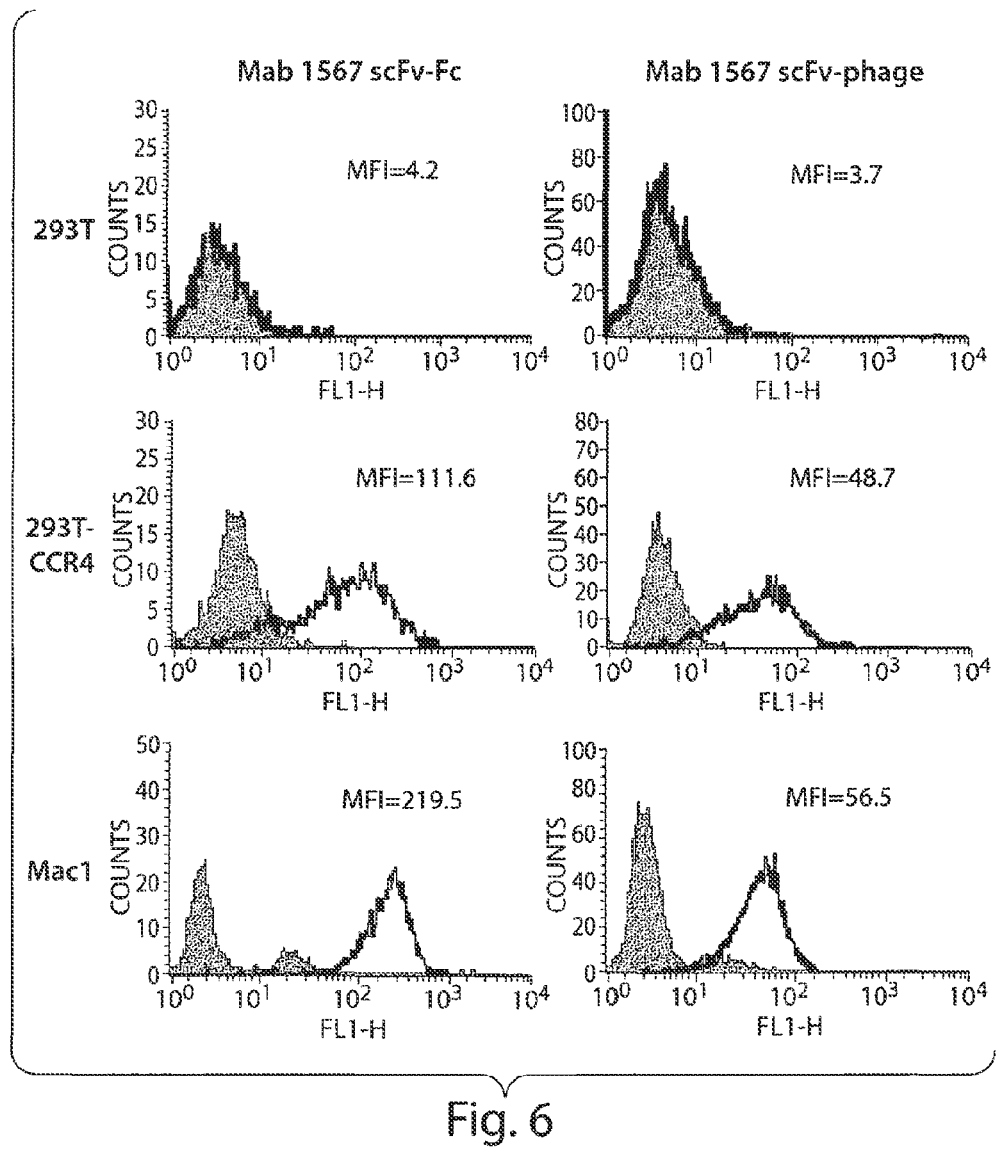
FIG. 6 are schematics showing FACS analysis of binding of 1567 scFv/scFvFc. The scFv gene of anti-CCR4 Mab 1567 was cloned into a phage display comprising either vector or Human IgG1 Fc-tagged expressing vector to express Mab 1567 scFv-phage and scFvFc. The specific binding of these two types of antibody to CCR4 was examined by FACS using CCR4$^+$ cell lines 293T-CCR4 and Mac-1 cells. Filled blue areas represent Negative scFv-phage or negative scFvFc control. Open, solid green outlined areas, represent Mab 1567 scFv-phage or scFvFc.

The murine anti-human CCR4 single-chain antibody (1567) was constructed from the hybridoma cell clone 205410 (provided by R&D systems Inc.) using known techniques. As shown in FIG. 6, 1567scFv binds specifically to Mac-1 cells as well as stable 293T-CCR4 cells but not to parental control 293T cells. Moreover there is a 2-4 fold increase in apparent affinity in converting the scFv to the soluble bivalent scFvFc (scFv-Hinge-CH2-CH3 of human IgG1).

Example 8

Expression of CCR4-Nt-Fc Fusion Protein for Epitope Mapping of 1567 Mab

Figure 7:
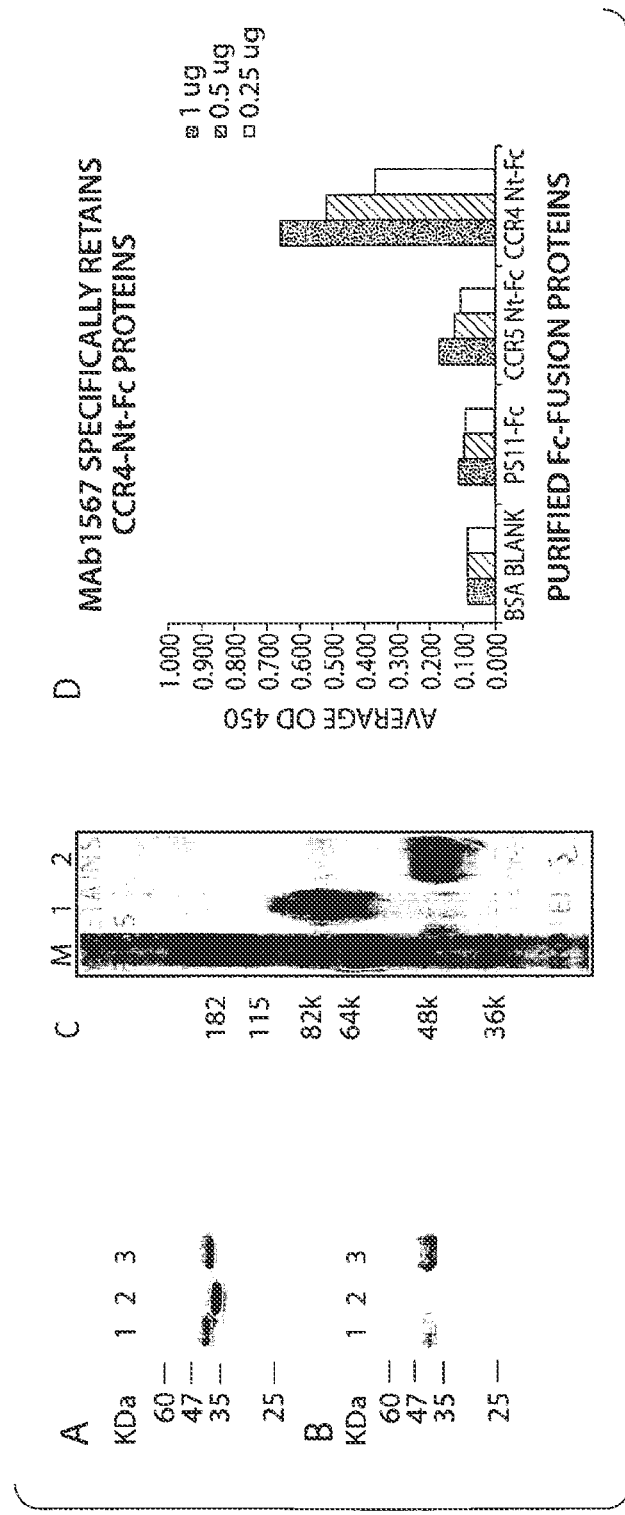
FIG. 7 are photographs of a Western Blot showing the expression of CCR4-Nt-Fc fusion protein and epitope mapping of Mab 1567.
Left Panel, 293T cells expressing F105-L3-Nt-hCCR4-Fc fusion protein were labeled with [$^{35}$S]-cysteine and [$^{35}$S]-methionine (panel A) or [$^{35}$S]-sulfate (panel B). Secreted proteins contained within the culture supernatant were immunoprecipitated with protein A sepharose beads and applied to a SDS-PAGE reducing gel for analysis. Lane 1 and 2, WT or DDDD mutant version of CCR5 Nt-Fc fusion protein (negative controls); Lane 3, human CCR4 Nt-Fc. Middle Panel (panel C), silver staining of secreted CCR4-Nt-Fc on non-reducing (lane 1) and reducing (lane 2) gel showing the presence of dimeric and monomeric protein, respectively, with protein sizes demarcated by the marker (M) lane. Right Panel (panel D), ELISA with plate bound Mab 1567 and analysis of Mab 1567 binding to three different Fc fusion proteins (PS11 scFvFc, CCR5-Nt-Fc, and CCR4-Nt-Fc) or BSA at three different concentrations (0.25 µg, 0.5 µg, or 1.0 µg per well). Binding detected by horseradish peroxidase (HRP)-anti-human Fc IgG.

A fusion protein was constructed to join a soluble version of the NH-terminus of CCR4 with a human IgG1 Fc domain. To show that this fusion protein could be processed by a cell properly and undergo proper signal peptide cleavage, 293T cells expressing the F105-L3-Nt-hCCR4-Fc fusion protein were labeled with [³⁵S]-cysteine and [³⁵S]-methionine, or [³⁵S]-sulfate. Culture supernatants containing secreted proteins were immunoprecipitated with protein A sepharose beads and applied to a SDS-PAGE reducing gel for analysis. The results indicated that the CCR4-Nt-Fc fusion protein had been secreted from transfected 293T cells following proper signal peptide cleavage. The wild type CCR5-Nt-Fc, used as a positive control, and the constructed CCR4-Nt-Fc proteins were also properly modified by post-translational processing demonstrated by sulfation of the tyrosine residues (Y16, Y19, Y20 and Y22) in the N-terminal (Nt) regions. However, the mutant CCR5 protein, used here as a negative control, in which 4 Nt tyrosine residues have been mutated to aspartic acid (DDDD), was not sulfated. The CCR4-Nt-Fc fusion protein is about 110 kDa and dimeric (bivalent) (FIG. 7).

The CCR4-Nt-Fc fusion proteins were also used to map the epitope recognized by 1567mscFv-Fc. ELISA experiments showed that the 1567 Mab specifically retained the CCR4-Nt-Fc protein, but did not bind the CCR5-Nt-Fc, an unrelated scFvFc (PS11) protein, or BSA. Thus, these data show that the Mab1567 specifically recognizes the N-terminus of CCR4, however, the possibility remains that the epitope encompasses multiple domains, one of which is the N-terminal region.

Example 9

Inhibition of CCL22-Mediated Chemotaxis by m1567 Mab and 1567 mscFv-Fc

The 1567 Mab and 1567 mscFv-Fc antibody were tested to assess their ability to inhibit CCL22-mediated chemotaxis of human ATCL tumor cells, Mac-1 cells. CCL22 is a well-characterized ligand for CCR4 that is expressed on T-cells. Mab1567 (10 ng/mL & 20 ng/mL), 1567 mscFv-Fc or an IgG2b isotype control were placed in the upper chamber of a 12-well transwell plate (of 5 µm pore size) in the presence of CCL22 (100 nM) in 600 µL media housed in the lower chamber at 37° C. for 4 hours. Cell migration into the lower chamber was determined by a FACS cell count using Flow-Check Fluorospheres as reference (experiments performed in duplicate). The migration assay results showed that both Mab1567 and 1567 mscFv-Fc inhibited chemotaxis of human Mac-1 tumor cells at very low antibody concentrations (ng/ml). Expectedly, the negative control isotype Mab had no effect.

Example 10

1567 mscFv-Fc-Mediated ADCC Activity

Figure 9:
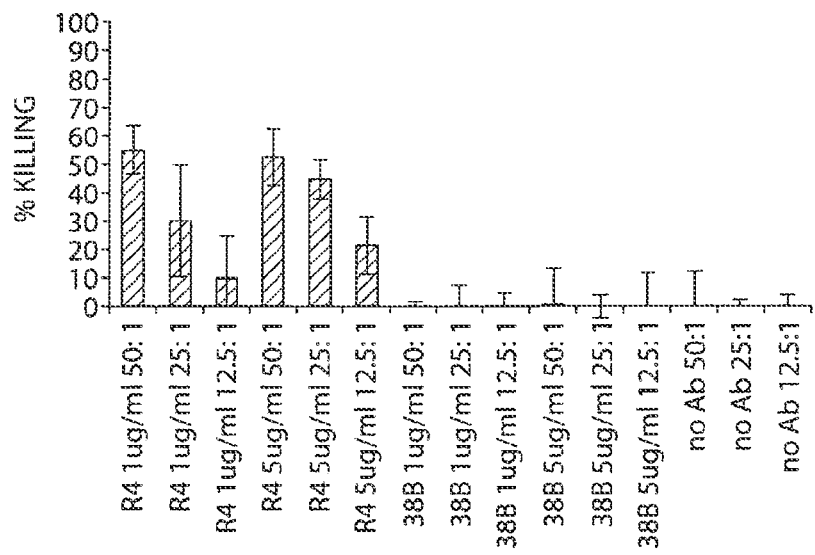
FIG. 9 is bar chart showing ADCC activity of 1567scFvFc. The CCR4 scFvFc (R4) and HA-1 scFvFc (38B) antibodies were used at concentrations of 1 ug/ml and 5 ug/ml, separately. Ratios of effector cells (PBMC) to target cells (Mac-1) (50:1, 25:1, 12.5:1) were used. Trials were performed in triplicate wells in a 96-well plate.

An ADCC assay was performed using the DELFIA EuTDA cytotoxicity kit. Normal, healthy, donor blood was obtained from Children's Hospital Blood Bank and peripheral blood mononuclear cells (PBMCs) were isolated via Ficoll (two different human PBMC donors were tested, only one of which is shown). Briefly, the target cell line, Mac-1, was labeled with fluorescent ligand BATDA reagent. Labeled Mac-1 cells (at a density of 11×10⁴/well) were loaded into a 96-well plate in triplicates (FIG. 9). Different ratios (50:1, 25:1, and 12.5:1) of effector (PBMCs) to target cells (labeled Mac-1 cells) were established within each set of triplicate wells. Anti-CCR4 1567 mscFv-Fc ("R4", in figure) or an irrelevant anti-HA 38B scFvFc ("38B", in figure) were added to each well at a concentration of 1 ug/ml or 5 ug/ml and incubated for 4 hours. The spontaneous release control was established by culturing the labeled cells in the absence of any other factor while the maximum release control was established by adding lysis buffer to labeled cells.

The results showed that anti-CCR4 1567 mscFv-Fc induces significant ADCC-mediated target cell death in all cases, however the effect was most extreme when the effector-to-target ratio was 50:1, halved in the 25:1 case, and present in 12.5:1 case. Anti-CCR4 1567 mscFv-Fc appeared to be as effective at 1 ug/ml as it was at 5 ug/ml. Neither anti-HA 3B3scFvFc nor the ab-free negative control displayed any ADCC activity. These studies demonstrate that the 1567 mscFv-Fc antibody mediates potent ADCC activity via CCR4 expressed on human ATCL tumor cells (Mac-1 cells).

Example 11

Construction and ADCC Activity of a Chimeric Human IgG1 Mab (cIgG)

Figure 10:
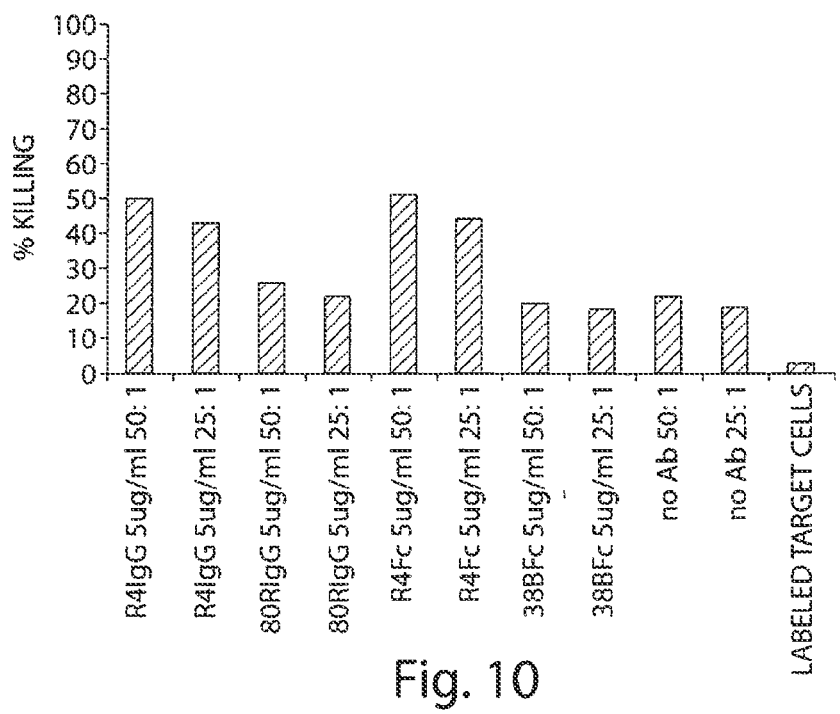
FIG. 10 is a bar chart showing ADCC activity of 1567IgG and 1567scFvFc. The target Mac-1 cells were pre-labeled with APC dye TFL4 (OncoImmunin, Inc.) for 1 hour at 37° C. The effector cells (PBMC) to target cells were mixed at ratios of 50:1 and 25:1, and centrifuged. The cell pellets were resuspended in fluorescien isothiocyanate (FITC)-caspase substrate and the antibodies were added at concentrations of 5 ug/ml and 25 ug/ml (not shown), separately. The assay was incubated for 2 hours at 37° C. After washing, the cells were analyzed by FACS. The CCR4IgG (R4IgG) and CCR4scFvFc (R4Fc) test antibodies, and irrelevant control 80RIgG and 38BscFvFc antibodies were included in the assay.

The individual VH and VL genes from murine 1567 scFv were used to construct a chimeric human IgG1 Mab (cIgG). A repeat ADCC assay was performed in order to compare the activities of the 1567 mscFv-Fc and 1567 cIgG. Although the background ADCC-mediated killing with the irrelevant 80R hIgG (anti-SARS antibody) or 3 8B scFvFc was high in this experiment, the 1567 (R4) cIgG and scFvFc treatments resulted in much higher ADCC activity (FIG. 10). Importantly, the ADCC activity of 1567 cIgG was at least as potent that of 1567 mscFv-Fc

Example 12

1567 cIgG Blocks Treg Activity

CD4$^+$CD25$^{high}$ (regulatory) and CD4$^+$CD25$^-$ (effector) T cells were either mono- or co-cultured (1:1 ratio, 2500 cells/well in both conditions) with irradiated CD3-depleted PBMCs (to present antigen), and exposed to either 1567 cIgG or control 80R hIgG (anti-SARS Mab) added into the medium. Following exposure to antibody and stimulation by anti-CD3 or anti-CD28, T-cell cultures were sorted by FACS and proliferation was measured on day 5 by $^3$H-labelled thymidine incorporation using a scintillation counter. The percent proliferation was normalized to CD4$^+$CD25$^-$ T effector cells without antibody treatment.

Figure 11:
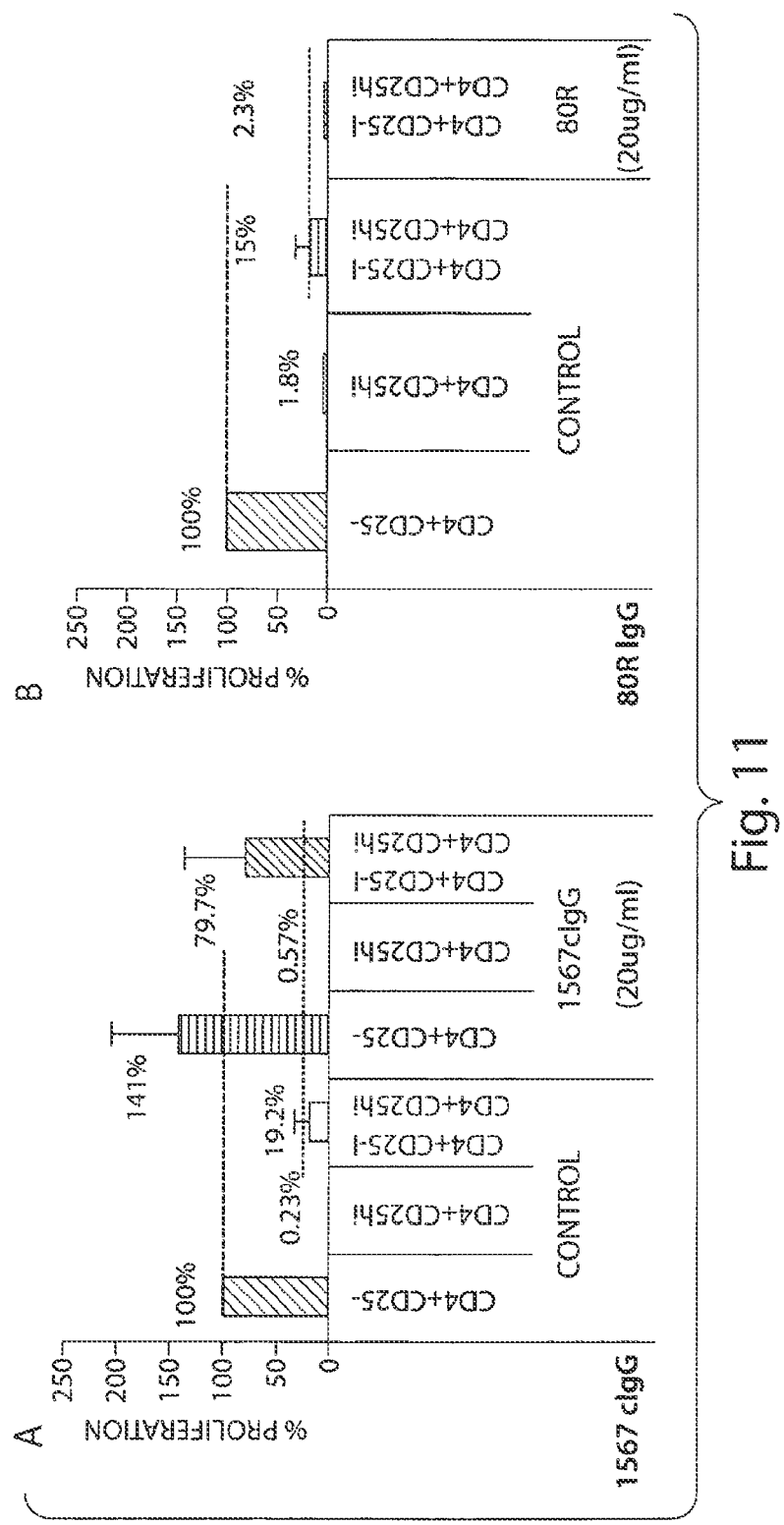
FIG. 11 are bar charts showing proliferation of mono- and co-cultures of regulatory and effector T cells in presence of 1567scFv, 1567 cIgG1 (panel A) and control (80R IgG1) antibodies (panel B). The CD4$^+$ T cells were sorted into CD4$^+$/CD25$^{high}$ (Regulatory) and CD4$^+$/CD25$^-$ (Effector) T cells by FACS. The Tregs and effector T cells were cultured at a density of 2500 cells/well either alone or as a 1:1 co-culture with 25,000 irradiated (3000 rad) CD3-depleted PBMCs used as antigen presenting cells (APC). The cultures were stimulated by 0.05 µg/ml peripheral blood anti-CD3 and 1 µg/ml soluble anti-CD28. Proliferation was measured on day 5 by $^3$H-labelled thymidine incorporation using a scintillation counter. The percent proliferation was normalized to CD4$^+$/CD25$^-$ T-effector cells without antibody treatment.

The results of this experiment showed that addition of the 1567 cIgG antibody augmented proliferation of CD4$^+$/CD25$^+$ (T effector cells (141%) compared to the proliferation of T effector cells without antibody treatment (FIG. 11). Importantly, 1567 cIgG dramatically reversed the suppression of T effectors by Tregs from 19.2% to 80% of the proliferation seen with untreated T effector cells. This abrogation of suppression was not seen with control 80R hIgG (anti-SARS Mab). These results suggest that 1567 cIgG abrogates the suppressive activity of Tregs in co-cultures by acting on the CD4$^+$/CD25$^-$ effector T cells.

Example 13

Figure 12:
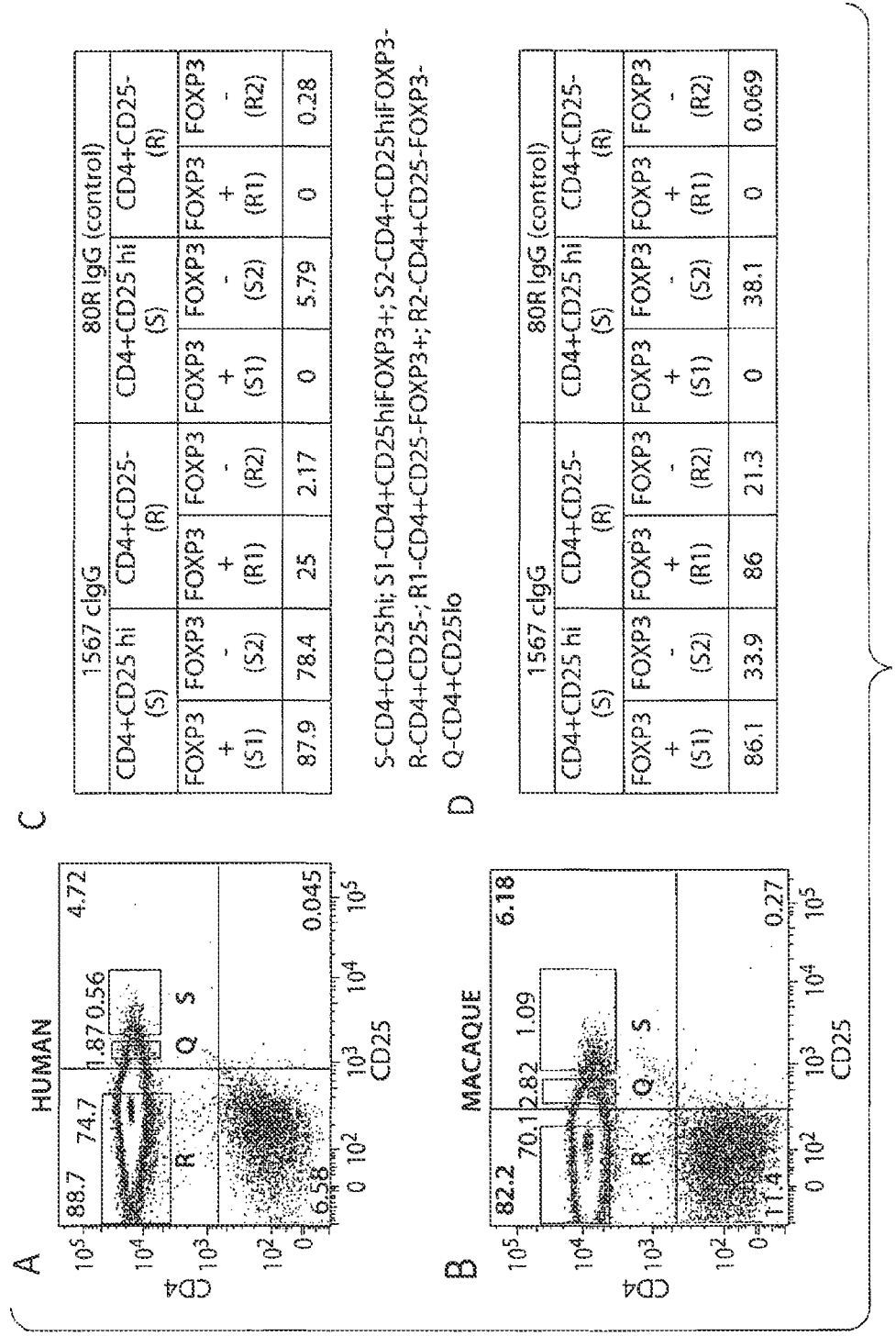
FIG. 12 are schematic of FACS scans showing binding of anti-human CCR4 (1567), chimeric IgG1, and 80R (control IgG1) to human (panel A) and macaque CD4$^+$ T Cells (panel B). CD4$^+$ T cells were incubated with 1567 cIgG or 80R IgG and then labeled with FITC-anti-human Fc specific secondary IgG. Cells were later stained for surface receptors CD4 and CD25, followed by fixation, and permeabilization for intracellular staining of FOXP3. Panels C and D enumerate binding of the respective cell types depicted in panels A and B.

1567 cIgG Binds to Human and Rhesus Macaque CD4$^+$ T Effector and Treg Populations FACS studies were performed on CD4 subpopulations from two human donors and rhesus macaques each, only one representative donor of each is shown in FIG. 12. The results showed that the 1567 cIgG bound to 88% of human CD4$^+$CD25$^{high}$Foxp3$^+$ cells with a phenotype consistent with Treg cells (see panel C of FIG. 12). A much lower percentage of 1567 cIgG binding to the human CD4$^+$CD25$^-$ cells was seen, which is consistent with previous observations that only a subset of CD4 memory T cells express CCD4. Similarly, CCR4 is expressed on 86% of CD4$^+$CD25$^{high}$Foxp3$^+$ rhesus macaque cells (see panel D of FIG. 12). However, in the two macaques that were studied, CCR4 staining of the CD4$^+$CD25$^-$ cells, both FoxP3$^+$ and FoxP3$^-$ populations was higher than was observed with human cells. The results suggest that rhesus macaques can be used as a close approximation of the human condition to develop a CCR4 Mab therapy.

Example 14

Humanization of VH from Mab1567

Figure 13:
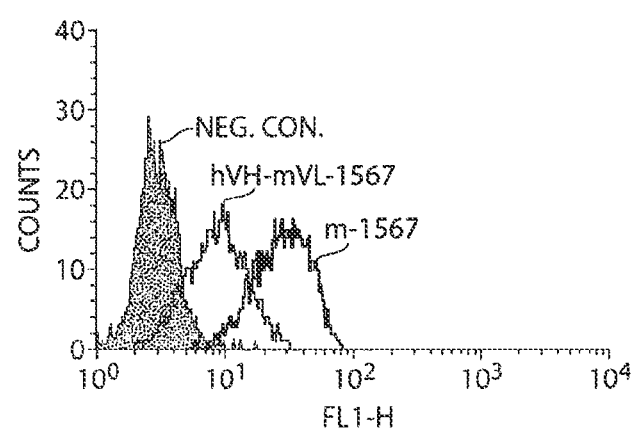
FIG. 13 are schematics showing FACs analysis illustrating the Humanization of Mab1567. The left panel shows FACS staining of the parental murine 1567 scFv-phage and the humanized Vh-mouse Vl hybrid scFv-phage. The right panel shows the binding of 3 of the 22 hybrid mouse Vh-human Vl scFv-phage that were isolated from the human VL chain shuffled library.

Three-dimensional modeling of the murine VH region was performed. A detailed all-atom model of the VH 1567 was constructed by using SwissModeling Software. Briefly, the best matched sequences of 1567 with known antibody structures in the Protein Data Bank (PDB) database were selected and used to building a reliable three-dimensional model of the variable regions. In parallel with modeling the structure, the amino acid sequence of mouse 1567 and human VH domains were compared in the Kabat database to find the most suitable human framework sequence for antibody humanization. A human VH framework sequence (McAb Ctm01, PDB: 1ae6H) with 82% homology to the mouse sequence was selected as the framework template for humanization of 1567 VH. Two other considerations were also taken into account during the VH humanization procedures: 1) key framework residues indicated by the three-dimensional model were kept and, 2) atypical amino acids that occur in less than 10-20% of the human VH genes were eliminated to avoid potential immunogenecity and were replaced with a consensus amino acid residue from the same human VH subgroup. A humanized VH gene (hVH) was designed and a human codon optimized gene was synthesized. Finally, a hybrid hVH-mVL of 1567 scFv was constructed and expressed as a phage-scFv to test its binding activity to the CCR4-expressing cell, Mac-1, by FACS (FIG. 13). The results of the FACS analysis showed that the hybrid hvh-mVL 1567 (half-human/half mouse) retains at least 50% of the mouse 1567 binding activity.

Example 15

Humanization of VL from 1567 MAb

Figure 14A:
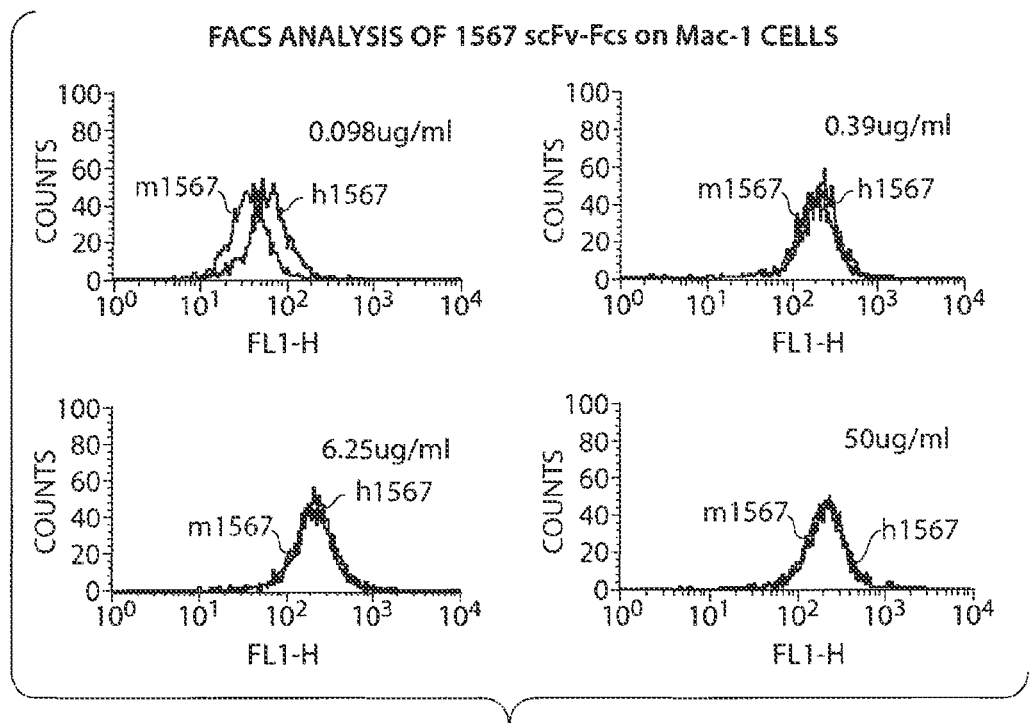
FIGS. 14A and 14B are a pair of graphs showing that upon comparing the binding activity of h1567-scFvFc to CCR4+ cell Mac-1 with mouse 1567, 1567mscFv-Fc, humanized 1567 still remained good binding activity to Mac-1 cells though not as good as m1567.
Figure 14B:
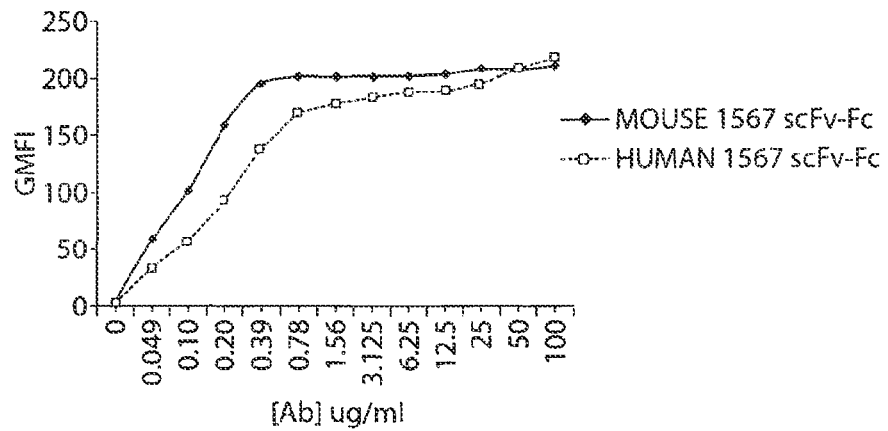

A similar strategy was used to humanize VL of 1567. A human Vkappa framework sequence (Genebank #ABG38372) with 84% homology to the mouse 1567 VL was selected as framework template for humanization. Thus, a humanized VH gene (hVH) and humanized VK gene (hVK) were designed and their codon optimized genes for expressing in human cells were synthesized, and then hVL of 1567 was paired with hVH of 1567 to form a fully humanized 1567 (567 hscFv). This scFv was further converted to soluble bivalent scFvFc (1567hscFv-Fc). Binding activity of h1567-scFvFc to CCR4+ cell Mac-1 was tested and compared with mouse 1567, 1567mscFv-Fc. As shown in FIGS. 14A and 14B, humanized 1567 still remained good binding activity to Mac-1 cells though not as good as m1567.

Example 17

Humanized VH and Human Full VL Library Shuffle

Light chain swapping is a powerful antibody technique that is used for both the humanization and augmentation of Mab binding affinity (Schier R. et al. J Mol Biol 1996, 255:28-43). It is possible that the humanized VH is not perfectly modeled from the murine VH, potentially resulting in some loss of binding activity when murine VH is exchanged for the humanized VH. Thus, a humanized VH-human VL shuffle library (1×10$^7$ member) was constructed to use in panning experiments with CCR4-PMPLs. Using this method, the library has a 1.2×10$^8$ human Vkappa available for shuffling. Positive clones showing strong Mac-1 binding properties are evaluated as described in Example 15.

Example 18

Human VH Shuffle Library with Optimized hVL

A human VL with the best binding activity from the above example is identified and used in combination with a human VH shuffle library to further enhance the binding affinity of the humanized antibody (Schier R et al. J Mol Biol 1996, 255:28-43). This library is on the order of $1\times10^8$ members (a $3.5\times10^8$ member human VH library is also available, see link in Example 16). This sequential chain swapping methodology is standard practice in the field and, importantly, the antibody that emerges from this screen has the same epitope specificity as the parental Mab. Panning is performed using CCR4-PMPLs. Evaluation of the phage binding to >70% of Mac-1 cells is performed in a manner identical to that described in Examples 15 and 16. A humanized 1567 Mab with an affinity of ≤1 $nM^{-1}$, which is a benchmark standard that is used in commercial Mab development, is produced using this strategy. This binding affinity allows hMabs 1567 to achieve therapeutically meaningful serum concentrations when dosed at ≤10 mg/kg/dose in humans.

Example 19

Optimization of Mab Binding Affinity Using Focused Mutagenesis

The combined results of Examples 15-17 and DNA sequence analysis of the CDR regions provide a pattern of consensus amino acids that play a significant role in binding activity. This information is used to further improve the binding affinity of the humanized 1567, if required, based on the cell binding and BiaCore binding studies (described in Example 21). Specifically, the pattern of conserved and variable amino acids provides valuable information for selecting which amino acids in the CDRs to subject to focused mutagenesis is concentrated on the variable amino acids surrounding the conserved amino acids that are uncovered in the analysis (Schier R et al. Hum Antibodies Hybridomas 1996, 7:97-105).

Example 20

Optimization of Mab Binding Affinity Using In Vitro Affinity Maturation

Higher affinity antibodies are obtained during the selection process by lowering the concentration of antigen in each subsequent round of panning (Marks JD. Methods Mol Biol 2004, 248:327-343). This modified panning procedure is used when needed and as guided by the results of the BiaCore studies described herein. (Schier R et al. Hum Antibodies Hybridomas 1996, 7:97-105).

Example 21

Cell Binding Affinity Measurements of Anti-CCR4 scFvFcs and IgGs

Saturation binding studies on stable $Cf2\text{-}CCR4^+$ cells are performed on each of the purified 1567 scFvFc and IgG variants. The approximate affinity of each antibody for CCR4 is measured by serially diluting each purified antibody prior to staining $Cf2\text{-}CCR4^+$ cells. The ability of the purified antibodies to bind to other CCR4 expressing cell lines, which express different conformations of CCR4, is also examined Cell lines used in this procedure include Mac-1 cells, $293T\text{-}CCR4^+$ cells, $CEM.NKR.CCR4^+$ cells, $HeLa\text{-}CD4^+/CCR4^+$ cells and $Ghost\text{-}CD4^+/CCR4^+$ cells.

Example 22

Affinity Measurements of Anti-CCR4 scFvFcs and IgGs Using BiaCore

The equilibrium dissociation constants ($K_D$) of 1567 scFvFc and IgG variants are determined by surface plasmon resonance on a BIACORE T-100 instrument using the BIACORE Pioneer L1 chip, which has been designed to work with lipid bilayers for the study of trans-membrane proteins. This biosensor chip has a carboxymethylated dextran matrix that has been modified with lipophilic substances and designed to capture liposomes rapidly and reproducibly (Stenlund P. et al. Anal Biochem 2003, 316:243-250; Navratilova I. et al. Anal Biochem 2006, 355:132-139; Navratilova I. et al. Anal Biochem 2006, 353:278-283; Navratilova I. et al. Anal Biochem 2005, 339:271-281). The capturing process permits the liposome to retain the lipid bilayer structure in such a way that injected liposomes can carry membrane-anchored molecules that protrude on one, or both sides of the lipid bilayer. The optimal conditions for immobilizing the Pioneer LI chips with purified hCCR4 PMPLs is pre-determined by using three different coupling buffers at standard running conditions. Association rates are measured using a constant flow of 5 µl/min and sFvFc and IgG concentrations ranging from $5\times10^{-6}$ to $1\times10^{-9}$ M. $K_{on}$ is determined from a plot of ln (dR/dt)/t vs. concentration (Karlsson R. et al. J Immunol Methods 1991, 145:229-240). Dissociation rates are measured using a constant flow of 25 ul/min and scFvFc/IgG concentration of $1.0\times10^{-6}$ M. $K_{off}$ is determined during the first 30 seconds of dissociation. $K_D$ is calculated as $K_{off}/K_{on}$.

Example 23

In Silico Modeling of 1567 VH and VL

The humanization of the mouse Mab 1567 is approached from several different directions to ensure the optimal result, which is an antibody with a resulting binding affinity of ≤1 $nM^{-1}$. In silico modeling of VH1567 is modified, with particular attention paid to the amino acids at the framework-CDR boundaries, which can be altered to provide greater flexibility in the binding site. New mutants of the initially modeled VH are produced by site-directed mutagenesis and retested for their binding affinity.

In silico modeling of the VL is completed in a similar manner to VH, and then used as a template for the humanization processes described in herein, including VH swapping studies. AMBER software (Assisted Model Building using Energy Refinement) is used for this modeling work.

Example 24

Epitope Mapping of Mab 1567 Using hCCR4 Mutant or Chimeric Proteins

For all subsequent epitope mapping descriptions, the humanized 1567 antibody is evaluated in the form of highly-purified soluble scFvFc and IgGs isolated from supernatants of transfected 293T cells. The methods used for identifying the epitope region are described here.

A series of hCCR4/hCCR2 chimeras by blunt-end ligation are constructed. hCCR2 has 45.6% a.a. sequence homology with hCCR4. A similar approach has been established for the construction of hCCR5/hCCR2b and hCXCR4/CXCR2 chimeras (Lee B. et al. J Biol Chem 1999, 274:9617-9626; Baribaud F. et al. J Virol 2001, 75:8957-8967). The N-terminus (Nt) and extracellular loop (ECL) regions 1, 2 and 3 of hCCR4 and hCCR2 are PCR amplified and blunt ligated. Using the designation of "4444" to represent the wild type (WT) CCR4 Nt, ECL1, ECL2 and ECL3, and "2222" to represent the WT CCR2 Nt, ECL1, ECL2 and ECL3, a complete series of chimeras are constructed that contain different Nt or ECL segments of the two chemokine receptors (e.g. 2444, 4244, 4424, etc.). This strategy enables the identification of linear, conformationally sensitive, and discontinuous epitopes on CCR4. All WT and chimeric expression plasmids contain a 3 amino acid tag to normalize surface protein expression by FACS analysis. For these studies, 293T cells are transfected with WT or chimeric constructs. Purified 1567 antibody is contacted to cells at a concentration of 50 µg/ml, followed by the addition of a fluorescently labeled antibody, phycoerythrin (PE)-labeled anti-IgG. The mean channel fluorescence (MCF) is used to compare the levels of antibody binding. Results are normalized for the MCF obtained for antibody binding to WT CCR4 (normalized as 100%) after subtraction of the background MCF obtained against empty vector-, pcDNA3, -transfected cells (normalized as 0%).

A series of N-terminal deletion mutants ($\Delta 4$, $\Delta 8$, $\Delta 12$ and $\Delta 16$) are used to define the precise region to which Mab 1567 binds. Furthermore a series of CCR4 point mutations, located within the Mab 1567 binding region, are generated by substituting the uncharged residue, alanine, for charged amino acids to identify residues that are important for binding. Charged amino acids that serve a critical binding function in the WT CCR4 epitope region demonstrate a loss-of-function, or loss of binding, when substituted for alanine. In addition to FACS analyses, Western blotting techniques are used to determine if the Mab 1567 antibody, when bound to WT, chimeric, or mutant hCCR4, recognizes linear or conformational epitopes (Lee B. et. al. J Biol Chem 1999, 274:9617-9626).

Figure 15:
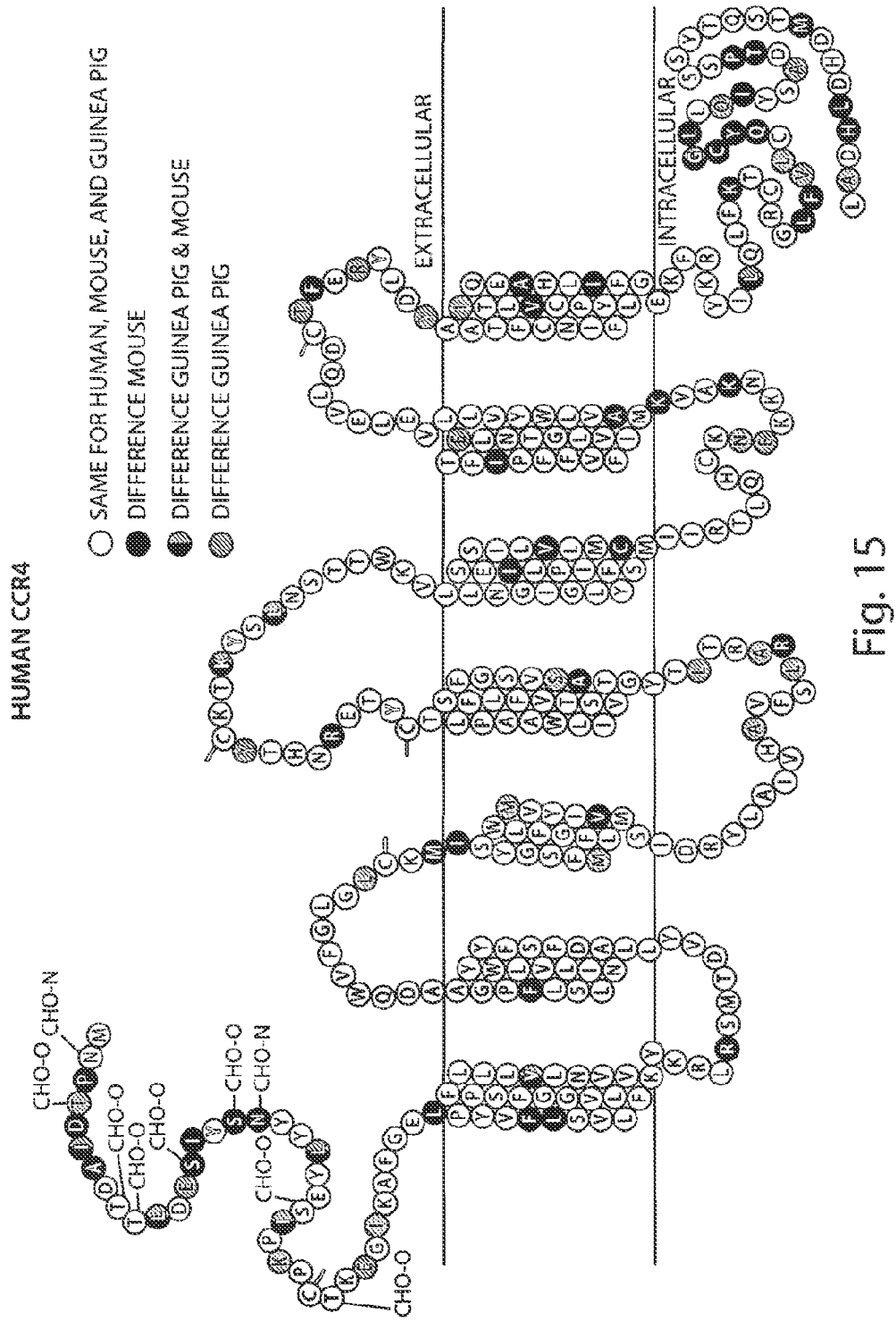
FIG. 15 is a schematic drawing of hCCR4. Differences in amino acids between human and mouse are black circles, differences between human and guinea pig are green circles, and differences between guinea pig and mouse are half black/green circles. Also shown are putative N and O glycosylation sites and tyrosines "Y" that may undergo post-translational sulfation.

Epitope mapping studies are performed by analyzing the binding of Mab1567 to mouse and guinea pig CCR4, which show high homology to human CCR4, except in the N-terminal region (FIG. 15). CCR4 is also cloned and PCR amplified from PBMCs sampled from cynomolgus and rhesus macaques housed within the New England Regional Primate Research Center. PCR primers are designed against the 5' and 3' flanking regions of human CCR4 in order to obtain unbiased sequence data at the beginning and end of the open reading frame (ORF). In all cases, the ORFs are stably expressed in Cf2 cells following G418 selection. The cross-reactivity of Mab 1567 to other human CCR and CXCR chemokine receptors will be tested. Exemplary chemokine receptors used to test cross-reactivity include: CXCR1, CXCR2, CXCR4, GPR1, GPR15, Str133, Dez, Apj CX3CR1, CCR1, CCR2B, CCR3.

Example 25

Mab 1567-Mediated Inhibition of CCR4 Ligand Binding

Recombinant CCL17 and CCL22 binding to WT and chimeric CCR4 are characterized to identify critical ligand-binding domains. First, CCL17-Fc and CCL21-Fc fusion proteins are constructed. FACS analyses are performed in order to detect receptor-ligand binding events using a FITC-conjugated anti-human IgG1. Transfected cells are incubated with the chemokine fusion protein, ligand, that binds to these cells via either the WT or chimeric CCR4 receptor. Stable Cf2-CCR4$^+$ cells are used to test the ability of the Mab1567 antibody to block binding of the ligands, CCL17 and CCL22, to CCR4-expressing cells. The ability of Mab1567 to block binding is determined by either the loss of median fluorescence intensity (MFI) or the percentage of fluorescently-labeled, or positive, cells. Positive controls include unlabelled recombinant CCL17 and CCL22 (Bioclon, Inc.). Non-specific binding is determined as MFI bound in the presence of a 100-fold excess of unlabeled ligand.

Example 26

Figure 8:
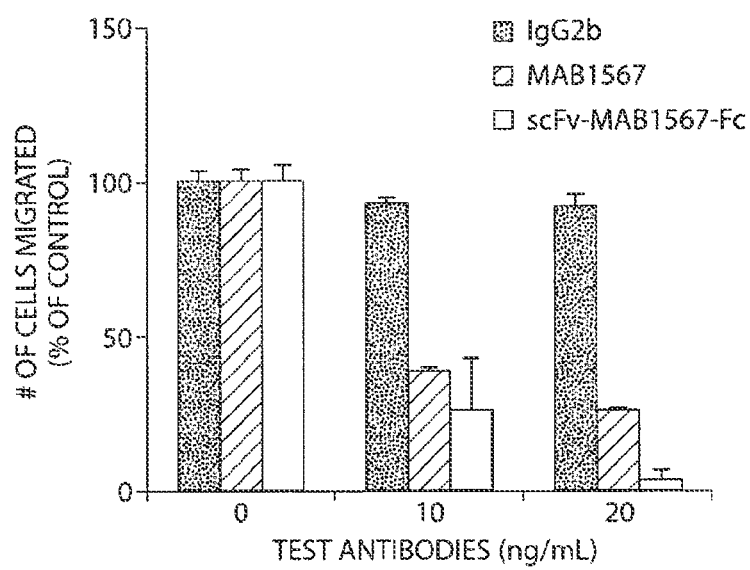
FIG. 8 is a bar chart showing the inhibition of CCL22-Induced Mac-1 Cell Chemotaxis by Mab1567 and scFv1567-hFc. 100 µL of Mac-1 cells (2×10$^5$ cells) were incubated with indicated concentration. Chemotaxis of human ATCL tumor cells, Mac-1, induced by the CCR4 ligand CCL22, is inhibited by both Mab1567 and the scFv1567-hFc at very low antibody concentrations. Mab1567 (10 ng/mL & 20 ng/mL), 1567scFvhFc, or an IgG2b isotype control were placed in the upper chamber of a 12-well transwell plate (of 5 µm pore size) while CCL22 (100 nM) was placed in 600 µL of media in the lower chamber at 37° C. for 4 hours. Cells migration into the lower chamber were determined by a FACS cell count using Flow-Check Fluorospheres as a reference (trials performed in duplicate).

Mab1567 Inhibition of CCL17/CCL22-Mediated PBMC Chemotaxis and Intracellular Calcium Mobilization Chemotaxis assays are performed with PBMCs in 24-well plates with transwell inserts of 5 µm pore size (Costar, Cambridge, Mass.). $5 \times 10^5$ cells are plated on the cover membrane in RPMI-1640 medium containing 0.4% fetal bovine serum and incubated at 37° C. For these studies a fixed optimal concentration of chemokine is used and serial dilutions of the Mab1567 are tested. Similar procedures are performed to evaluate the ability of the Mab1567 to block chemokine-mediated intracellular calcium mobilization. Calcium mobilization assays in PBMCs are performed using FURA-2 (Molecular Probes) (Juremalm M. et. al. Clin Exp Allergy 2005, 35:708-712). Fluorescence measurements are taken with a Hitachi F-2000 fluorescence spectrophotometer using the dual-wavelength optional function at wavelengths 340/380 nm (excitation) and 505 nm (emission). Data points are collected every 500 ms and recorded as the relative ratio of fluorescence excited at 340 and 380 nm. The ability of the Mab1567 to block CCL17/CCL22-mediated chemotaxis and intracellular calcium mobilization is also tested in Sezary cells from patients. The results show that the Mab1567 antibody blocks chemotaxis mediated by CCL22 (FIG. 8).

Example 27

Mab1567-Mediated Depletion of CCR4-Bearing Cells

The ability of Mab1567 to deplete CCR4-bearing cells is tested in multiple in vitro and in vivo assays. For the in vitro assays, Mab1567 is secreted from transiently-transfected 293T cells and purified by protein A chromatography. For in vivo assays, the experimental mice are manipulated to produce Mab1567 antibody via AAV-8-mediated gene transfer. A method was devised to assess the in vivo depletion of PBMC by utilizing magnetic beads to efficiently eliminate CCR4$^+$ cells from PBMC in vitro. This strategy yields a meaningful result without prior knowledge of which potential Mab 1567-mediated mechanism executes CCR4 depletion in vivo.

In this example, Dynabeads® Pan Mouse IgG magnetic beads (Dynal product #110.41) are produced with a coating of a single Mab that recognizes all classes of mouse IgG, but does not cross-react with any class of human-derived antibodies. These beads are "charged" with a mouse-anti-human IgG1 Mab (SouthernBiotech product #9052-01), so that they bind to any cell that has been coated with human IgG1, or in this case, any cell that binds the Mab 1567.

The granulocyte types, naïve T cells, B cells or NK cells are used as negative controls in this study because it is known that these cell populations do not express CCR4 (Campbell J. J. et al. Nature 1999, 400:776-780). Based upon levels of CCR4 expression, Mab1567 is expected to deplete a significant proportion of memory T cells and Treg cells. Recent publications by those skilled in the art suggest that this type of cell is responsive to CCR4 ligands (Hirahara K. et al. J Immunol 2006, 177:4488-4494; Iellem A et al. J Exp Med 2001, 194: 847-853) (FIGS. 11 and 12). Treg cells are believed to play a role in immunotolerance to neoplastic cells (Abbas A, Lichtman, A H. Cellular And Molecular Immunology, Updated Edition (ed 5). Elsevier Saunders 2005). Therefore elimination of these cells mediated by Mab 1567 supplements existing mechanisms that directly eliminate leukemic CTCL cells and dramatically increase the effectiveness of Mab1567 in arresting the progression of CTCL.

It is not unprecedented that chemokine receptors exist with post-translational modifications in different cell types (Hill C. M. et al. Virology 1998, 248:357-371). The results of these depletion assays are screened to find these differences, as well as conformational heterogeneity within CCR4 proteins.

Example 28

Mab1567-Mediated Apoptosis Induction of CCR4$^+$ Cells In Vitro

The ability of MAb1567 to induce apoptosis of CCR4-expressing cells after cross-linking with a secondary antibody is examined. Mac-1 cells in exponential growth phase (grown in supplemented RPMI with 10% bovine serum) are incubated with Mab1567 or with the negative control IgG1 hMab on ice. These cells are then washed and incubated again on ice for 1 hour with F(ab')2 fragments of goat-anti-human IgG (heavy and light chain specific, Jackson ImmunoResearch product #109-006-003). Next, cells are centrifuged, washed, and resuspended in Mac-1 culture medium at 37° C. Incubation proceeds for 2 hours to allow any signal transduction to occur that might result from CCR4 cross-linking. After incubation, the cells are washed and resuspended in cold medium.

Whether or not cross-linking of CCR4 induces apoptosis is assessed using an annexin V-based apoptosis detection procedure (Annexin V-FITC Apoptosis Detection Kit II, BD Pharmingen product #556570). This assay is based on the finding that annexin V binds to phosphatidylserine (PS), which is only associated with the internal membrane components of healthy cells, but, as a result of compromised membrane homeostasis, appears on the cell surface during apoptosis. Thus, a cell that stains with FITC-conjugated annexin V but is still intact (as assessed by propidium iodide (PI) exclusion) and is in the early stages of apoptosis. Cells in late stages of apoptosis stain with both FITC-conjugated annexin V and PI.

Other CCR4-expressing cell-types available for these assays (e.g. stable Cf2-CCR4 and 293T-CCR4 cells) are tested in parallel with Mac-1 cells to circumvent complications arising from a potential insusceptibility of Mac-1 cells to apoptosis. Furthermore, primary PBMCs are included in this assay (although a negative control other than CCR5, e.g. human anti-HA 3B3 IgG, is utilized in this case), and, PBMC from leukemic CTCL patients are tested.

Example 29

Mab1567-Mediated Depletion of CCR4$^+$ Cells by ADCC In Vitro

The ability of Mab1567 to target CCR4-expressing cells for destruction via ADCC is assessed. The DELFIA EuTDA cytotoxicity kit, as described in FIGS. 9 and 10, is used to detect cytotoxicity. Of particular physiological relevance, the ability of Mab1567 to trigger ADCC responses with human effector cells is examined. It is necessary to optimize conditions separately for human PBMC and mouse splenocytes. The anti-CD30 antibody, already known to robustly bind Mac-1 cells (Kleinhans M. et al. Blood 2003, 101:1487-1493), is employed for optimization of target:effector ratios and other parameters required for utilization of the DELFIA kit.

Mac-1 cells are treated with Mab1567 or a negative control Mab. These cells are washed and resuspended in culture medium with the optimized number of human PBMCs and incubated for 4 hrs at 37° C. All conditions are repeated in triplicate wells. The level of cell death achieved for anti-CCR4-treated cells is compared to that of control-treated cells. The control for spontaneous release is prepared by culture of the labeled cells only and the control for maximum release is obtained by adding lysis buffer to the labeled cells.

Other cell types including stable Cf2-CCR4 and 293T-CCR4 cells are examined to determine the effect of CCR4 surface density on cell killing because these cells express lower levels of CCR4 compared to Mac-1 cells. Primary PBMCs are tested in this assay (anti-HA 3B3 Mab is utilized at negative control in this case), and, PBMCs from leukemic CTCL patients are tested as target cells when available.

Example 30

Mab1567-Mediated Depletion of CCR4$^+$ Cells by Complement-Mediated Lysis In Vitro The ability of Mab1567 to target CCR4-expressing cells for destruction by the complement system is examined Complement-mediated cell damage is assessed by the DELFIA EuTDA cytotoxicity kit. Guinea pig complement (lyophilized, Rockland Immunochemicals product #C200-0005) is prepared fresh for each experiment. Mac-1 cells are coated with either Mab1567 or negative control Mab, washed, and resuspended in low-serum medium in 96-well plates. Freshly prepared guinea pig complement is added to each well at the optimal concentration, and the plates are incubated at 37° C. for 30 minutes. The level of cell death for anti-CCR4-treated and control-treated cells is compared.

Example 31

Mab1567-Mediated Depletion of CCR4$^+$ Cells by ADCP In Vitro

The ability of Mab 1567 to enhance the phagocytic activity of monocytes and macrophages, a process called antibody-dependent cellular phagocytosis (ADCP), is assessed. Human monocytes/macrophages are separated from human PBMCs by negative selection with anti-CD3-, CD19-, and CD56-based magnetic cell sorting. Mac-1 target cells are incubated with the lipophilic fluorochrome PKH26 (Sigma), mixed in a 1:5 ratio with monocytes/macrophages, and co-cultured with either Mab1567 or control Mab at 10 ug/ml. Following a 1 hour incubation at 37° C., the cells are harvested by EDTA, residual Fc receptors are blocked with rat serum (DAKO), and the monocyte/macrophages are stained with FITC-conjugated anti-CD14 Mab. The spontaneous phagocytosis is calculated from cultures lacking Mab1567 but containing control Mab. The mixture of PKH26-labeled Mac-1 cells and human monocyte/macrophages is stained also with FITC-conjugated anti-CD 14 Mab, without pre-incubation, and used as a control. Double-positive cells (PKH26/FITC) represent Mac-1 cells phagocytosed by the monocytes/macrophages.

Example 32

Mab1567-Mediated Depletion of CCR4$^+$ Cells by Blocking Ligand-Mediated Signaling Through CCR4 In Vitro Primary CTCL cells are difficult to grow in culture. In fact, reliable tissue-adapted CTCL lines are not currently available. Although, malignant cells can now be directly isolated from skin lesions. This culture obstacle is likely due to the fact that growth factors available in vivo have not been adequately provided by the culture conditions tested to date. CCR4 is remarkably persistent on leukemic CTCL cells, despite frequent loss of other crucial skin-homing molecules. One intriguing explanation for this persistence might be a dependence on CCR4 signaling to provide necessary pro-growth signals for in vivo. Therefore, the ability of CTCL cells to survive in culture was tested in the presence of soluble CCR4 ligands. If ligand-CCR4 interactions promote in vitro survival, the ability of Mab1567 to block CCL17 and CCL22 binding to CCR4 can be used to inhibit growth of leukemic CTCL in vivo. The experiments used to test this therapeutic avenue are described below.

Primary CTCL cells isolated from leukemic CTCL patients are cultured in supplemented RPMI with 10% bovine serum among individual wells in 24-well plates with either recombinant CCL17 or CCL22 present at various concentrations, or in the absence of chemokines. Each chemokine is tested at concentrations 0.1×, 1× and 10× their interaction $K_D$ with CCR4. The cultures are monitored visually for differences among wells with regard to cell number. If greater numbers of cells are detected in wells that contain one of the CCR4 ligand concentrations, wider chemokine concentration ranges are tested in order to optimize the in vitro culture conditions for primary leukemic CTCL cells. Once the optimal CCR4-ligand-dependent growth conditions are established for primary leukemic CTCL cells, Mab1567 are tested at various concentrations in individual culture wells to determine if Mab treatment can block this proliferative effect. Similar experiments are performed with skin-derived CTCL cells.

Example 33

Mab1567-Mediated Depletion of CCR4+ Cells In Vivo

The ability of Mab1567 to prevent growth and/or mediate destruction of CCR4-expressing cells is assessed using a xenograft SCID/Beige mouse model. Based on the in vitro data generated above, the most potent humanized Mab 1567 is tested in the mouse model of CTCL. For these studies, both antibody gene transfer and protein injection methods are used to deliver therapeutic levels of Mab1567 in order to assess its ability to prevent tumor growth in a pre-implantation and post-tumor implantation Mab treatment study.

Example 34

AAV-8-Mediated Gene Transfer

Figure 16:
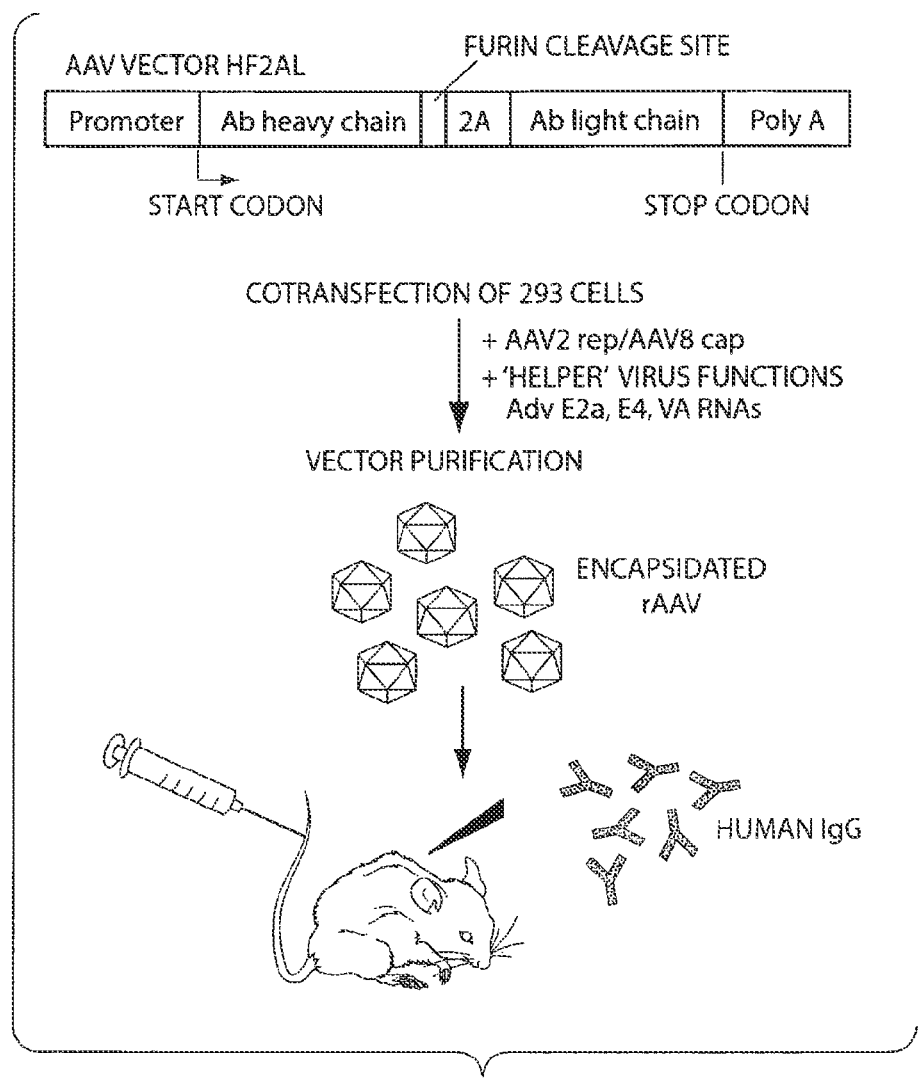
FIG. 16 is an illustration showing procedures for In Vivo Therapeutic Antibody Gene Transfer in Mice. Gene transfer is accomplished using a newly reported rAAV serotype 8 (AAV-8) vector.

A remarkably powerful technique has recently been reported, and modified by the Marasco laboratory, that can allow human Mabs to be expressed at therapeutic levels for prolonged periods of time (several months) following systemic delivery by a single intravenous injection of gene transfer vector (Marasco Wash. Nat Biotechnol 2005, 23:551-552) (see FIG. 16). Specifically, gene transfer is accomplished using a newly reported rAAV serotype 8 (AAV-8) vector. Recently isolated from rhesus macaques, this vector has the capacity to transduce hepatocytes and skeletal muscle with very high efficiency when delivered by portal vein injection or intravenous infusion (Nakai H et al. J Virol 2005, 79:214-224; Gao G. P. et al. Proc Natl Acad Sci USA 2002, 99:11854-11859). A recent report by Fang et al. (Nat Biotechnol 2005, 23:584-590) demonstrated that remarkably high levels (>1,000 ug/ml) and long-term expression (>140 days) of an anti-VEGR2 Mab could be achieved in mice and demonstrated therapeutic efficacy against two tumor cell lines in two mouse tumor models.

Example 35

AAV-8-Mediated Gene Transfer In Vitro

The AAV vector (pTR-UF20, gift of Dr. N. Muzyczka, Univ of Florida) has been modified to accommodate two types of antibodies, the bivalent scFv-Fc fusion proteins and whole human IgG1 Mabs. The latter utilizes the furin-2A-self cleavage cassette which results in stoichiometrically equivalent amounts of heavy and light chains. In both antibody configurations, interchain disulfide bonding is intact and fully functional bivalent molecules are secreted. This plasmid uses the CMV IE enhance, chicken β-actin promoter and intron sequences to drive high levels of antibody expression.

For the studies outlined here, rAAV vectors encoding Mab1567 IgG1 are used. The AAV-Mab1567 vector plasmid is co-transfected with the AAV2rep/AAV8cap packaging plasmid (p5E18-VD2/8, gift from Dr. J. Wilson, Univ of Penn)(Gao G. P. et al. Proc Natl Acad Sci USA 2002, 99:11854-11859) and the mini-adenovirus helper plasmid (pXX6-80, gift from Dr. J. Samulski, Univ North Carolina) (Xiao X. et al. J Virol 1998, 72:2224-2232) into subconfluent 293 cells using a calcium phosphate method. 48 hours after transfection, cells are harvested using PBS/EDTA (10 mM) and lysed by three freeze/thaw cycles in cell lysis buffer. Lysates are treated with 250 U/ml benzonase for 15 min at 37° C. and cellular debris is removed by centrifugation. The cleared cell lysate is fractionated by ammonium sulfate precipitation and the rAAV virions are isolated on two sequential CsCl gradients. The gradient fractions containing rAAV are dialyzed against sterile PBS containing CaCl2 and MgCl2, and stored at −80° C. Viral titers are determined by dot-blot analysis (Fang J et al. Nat Biotechnol 2005, 23:584-590). Each rAAV virion preparation is first tested in vitro on transduced 293 cells. The time course and level of antibody secretion are then analyzed by human IgG capture ELISA with reagents that recognize the Fc of IgG1, by cell based ELISA titers on stable CCR4+ cells, and by Coomassie blue staining on non-reducing and reducing SDS-PAGE gels of antibody that is purified from the supernatants by protein A-agarose beads.

Example 36

Prevention of New Tumor Implantation in a CTCL Mouse Model

The timing and levels of Mab1567 antibody expression in vivo are analyzed in pilot studies in SCID/beige mice. Briefly, groups of 8 mice, comprising a test cohort, are injected by the tail vein with rAAV8-Mab1567 ($1\times10^{11}$, $2\times10^{11}$ or $4\times10^{11}$ vector genomes (vg)/mouse) and antibody levels are analyzed over time by human IgG capture ELISA. Mice are subsequently bled by alternate retro-orbital puncture at each scheduled time point for up to 4 months for analysis of recombinant antibody expression. The results of these studies determine the optimal vector dose of Mab1567 that is required to achieve an expected therapeutic dose and the duration after vector administration, for which that dose should be achieved.

For the mouse tumor models, female SCID/beige mice (n=10-12 in each group) are injected with rAAV8-Mab1567 or rAAV8-control Mab virions via tail vein in 200 ul PBS at the optimal dose, as determined above. Mice in the negative control group are treated with the same dose of an anti-CCR5 Mab-encoding rAAV8 vector. To monitor human IgG1 levels, mice are bled weekly by alternate retro-orbital puncture. When steady state has been achieved, circa 21 days, the animals are inoculated with single-cell suspensions of the luciferase-expressing human cutaneous CCR4+ ALCL line Mac-1 ($2 \times 10^7$ cells) into the left flank of the mouse using a 13-gauge trocar. These cell lines have already been produced by transduction with MuLV-luciferase virus and stable high luciferase expressing subclones have been established. The size of the subcutaneous tumors are measured with a caliper and tumor volumes are recorded according to the formula $V = d \times D \times \pi / 2$, where d is the smaller diameter and D the larger diameter. Mice are monitored for tumor development and progression by both caliber measurement and Xenogen imaging. The latter, which allows monitoring of metastatic disease in living animals, is performed twice each week following intravenous injection of 50 mg/ml D-luciferin. Treated and control mice are eventually euthanized and necropsied for evidence of tumors. Post-mortem analysis of tumor formations includes histology and immunohistochemistry. Mice are euthanized when tumor diameter reaches 1.5 cm or when moribund. This procedure was repeated with additional cohorts of mice comprising a total of 24 mouse subjects.

In order to determine if Mab1567 has potent anti-tumor activity in vivo, non-parametric and parametric methods of analysis are used to compare human IgG1 levels between the negative control rAAV8-IgG1 and the experimental rAAV8-Mab1567 group. An adjustment is made for multiple pair-wise comparisons. It is anticipated that this experimental approach establishes that Mab1567 has potent anti-tumor activity in vivo. If potent anti-tumor activity is not observed and this result is not attributable to low serum levels of the Mab1567 protein, the conventional method of delivering antibody by intraperitoneal injection is preferred since this allows peak and trough antibody levels to occur which may have a positive effect on the ability of the immune system to clear the antibody bound tumor cells through FcγR-mediated mechanisms. In this event, the purified Mab1567 protein is injected by intraperitoneal injection 20 mg/kg scFvFc twice each week for up to 4 weeks. Alternatively, the heavy chain isotype of Mab1567 is changed to hIgG3 in order to increase complement-mediated tumor clearance. In this event, the isotype switch is performed and AAV8-Mab1567 virions are used to deliver the hIgG3 homolog.

Example 37

Destruction of an Existing Tumor in a CTCL Mouse Model

Destruction of an existing tumor in an established SCID mouse CTCL xenograft model is described. It is uncertain at the present time whether or not the kinetics of in vivo antibody production in the AAV8 gene transfer system are sufficiently robust to achieve therapeutic antibody concentrations in the time frame required to inhibit growth of existing tumors. Therefore, AAV8 gene transfer, protein injection, and a combination of these methods are used to deliver Mab1567 to mice with established tumors and the results of each attempt are compared.

These studies are conducted as described in Example 32 (SCID/beige mice in groups of 10-12) except that gene delivery and protein injection begin on days +1 and +5 after tumor implantation in order to assess the ability of Mab 1567 to inhibit early versus late tumor growth. Specifically, on day +1 (early tumor) or day +5 (late tumor), the animals are injected intravenously (i.v.) with AAV8-Mab1567 virions (single optimal dose) or intraperitoneally (i.p) with Mab1567 protein twice each week for the first 4 weeks. A third treatment group also receives both treatments beginning on day +1 or +5 however, in this group, only two i.p. injections of Mab1567 protein are used which provides an initial high serum concentration of antibodies until the gene transfer antibody reaches a therapeutic level. Control mice receive identical treatments with an isotype control Mab. Tumor growth is monitored in live animals by caliper measurements and Xenogen imaging. Histology and immunohistochemistry are performed on tissue harvested from sacrificed animals as described in the "detailed description" section of this application. This procedure was repeated with additional cohorts of subjects comprising 72 in total.

In order to determine if Mab1567 is able to inhibit the growth of early and late established CCR4+ ALCL tumors, non-parametric and parametric methods of analysis are used to compare the three groups treated with AAV8-Mab1567 vector, Mab1567 protein, or both AAV8-Mab1567 and Mab1567 protein, respectively. An adjustment is made for multiple pair-wise comparisons. It is anticipated that the experimental results obtained from these procedures demonstrate that Mab1567 is able to inhibit the growth of early and late established CCR4+ ALCL tumors. However, the CCR4+ ALCL cell line may not be predictive of the in vivo growth behavior of CCR4+ CTCL lines and the inhibition of their growth by Mab1567.

Example 38

Mab1567 Production in Chinese Hamster Overy (CHO) Cells

A high secretor CHO (DG44) transfectoma cell line is established and tens of milligrams quantities of Mab1567 are purified. The human immunoglobulin IgG1 kappa (TCAE5) expression vector is used to target mammalian loci that support high levels of expression. This vector encodes immunoglobulin heavy and light chain genes, the dihydrofolate reductase (DHFR) gene, and the dominant selectable marker neomycin phosphotransferase (Neo) gene. As a result of intentional impairment of the Kozak sequence surrounding the Neomycin initiation codon, included to create a fully impaired Kozak sequence, most single copy integrants do not express enough Neo to survive selection (Kozak M. J Mol Biol 1987, 196:947-950). The result is that the overall number of G418 resistant cells is greatly reduced, thereby facilitating screening. A higher percentage of the clones surviving selection are those in which the impaired Neo gene has been integrated into "hot spots" with the genome, which concomitantly yield very high levels of linked gene expression (Barnett R. L. et al. Antibody Expression and Engineering. Edited by Wang H Y IT, 1995, pp 28-40). Once isolated, transfectants which display a very high level of immunoglobulin protein production are induced to undergo gene amplification by selection with increasing concentrations of methotrexate (MTX) (5 nM→50 nM→500 nM) for the dihydrofolate reductase gene (Kaufman R J, Sharp P A. J Mol Biol 1982, 159:601-621). As the DHFR gene copy number increases through amplification, there is a parallel increase in the closely linked immunoglobulin gene copy number with an accompanying rise in immunoglobulin production. Amplification of initially very high level expression clones yields cells producing even greater levels of immunoglobulin protein from a minimal number of gene copies (Barnett R. L. et al. Antibody Expression and Engineering. Edited by Wang H Y I T, 1995, pp 28-40). At the 500 nM stage, the selected amplificants are readapted to grow in spinner flasks. During this time, transfectoma antibody is purified from the supernatants over protein A. When the cell is producing 100 pg/cell/day and has a doubling time of 36 hours or less, it is considered a production cell line and a Parent Seed Stock is prepared.

Example 39

Mab Production in YB2/0 Cells

One IgG molecule contains two N-linked oligosaccharides sites in its Fc region (Rademacher T. H. et al. Presented at the Biochem Soc Symp, 1986). The general structure of N-linked oligosaccharide of IgG is complex-type, characterized by a mannosyl-chitobiose core (Man3GlcNAc2-Asn) with or without bisecting GlcNAc/L-fucose (Fuc) and other chain variants including the presence or absence of Gal and sialic acid. In addition, oligosaccharides may contain zero (G0), one (G1), or two (G2) Gal. ADCC requires the presence of oligosaccharides covalently attached at the conserved $Asn^{297}$ in the Fc region and is sensitive to change in the oligosaccharide structure. Recent studies have shown that engineering the oligosaccharides of IgGs may yield optimized ADCC. In particular, the absence of fucose, but not the presence of galactose or bisecting N-acetylglucosamide of human IgG1 complex-type oligosaccharides, has been shown to play the critical role of enhancing antibody-dependent cellular toxicity (Shinkawa T. et al. J Biol Chem 2003, 278:3466-3473). Human IgG1 produced by rat hybridoma YB2/0 cells showed extremely high ADCC at more than a 50-fold lower concentration of those proteins produced by CHO cells. YB2/0 cells expressed a lower level of FUT8 ($\alpha$1,6-fucosyltransferse gene) and produced IgG1 of lower Fuc content compared to CHO cells (Shinkawa T. et al. J Biol Chem 2003, 278:3466-3473).

The hypothesis that ADCC contributes to Mab1567-mediated immunodepletion of $CCR4^+$ ALCL tumors in SCID mice is evaluated by comparing the in vitro and in vivo killing effects of anti-CCR4 Mab antibody produced in CHO and YB2/0 cells. An efficient transfection procedure for YB2/0 cells (Amixa kit) has been established. Thus, a high secretor cell line from YB2/0 is developed, as described for the CHO cell lines above. Again, when the cell is producing 100 pg/cell/day and has a doubling time of 36 hours or less, it is considered a production cell line and a Parent Seed Stock is prepared. Transfectoma antibody is purified from the supernatants over protein A. Tens of milligrams of total Mab from the high-secretor CHO and YB2/0 cell lines are produced for further in vitro and in vivo target validation studies.

Example 40

ADCC of ATCL/CTCL Cells In Vitro by Mab1567 with Differential Fucose Content

Mab1567 produced in Examples 35 and 36 is used to evaluate the role of ADCC in tumor cell killing in vitro. In brief, The cytotoxic activity of human PBMCs is determined using the DELFIA EuTDA cytotoxicity kit. Fifty microliters of target cells at $2\times10^5$ cells/ml are added to 96-well "U"— bottomed microtiter plates (Nunc) to achieve effector/target (E:T) ratios varying from 25:1 to 0.7:1. PBMCs are isolated with Ficoll-Pague Plus from buffy coats. Effector cell number in all assays is calculated based on the total number of mononuclear cells. Varying doses (50, 10, 1, 0.1, 0.01 µg/ml final concentration) of Mab1567 or negative control isotype matched Mab are tested. Background killing activity of target cells is concurrently measured by incubation of PBMCs with target cells in the absence of Mab. Each sample is measured in triplicate. Controls include spontaneous release (medium alone) and total release (10% Tween-20/PBS). It is expected that the YB2/0-produced Mab is more active than the CHO-produced Mab in this ADCC assay.

Example 41

ADCC in Tumor Prevention and Destruction in a CTCL Mouse Model

Potent anti-tumor activity of Mab1567 in the SCID/Beige model with Mac-1 xenografts were shown. Remarkably, a profound effect was seen despite the fact that these mice are devoid of NK cells which mediate ADCC. The ability of the Mab 1567 to prevent and destroy tumors is established in an alternative mouse model by using severe combined immunodeficiency (SCID) mice in order to evaluate the in vivo contribution of ADCC in tumor destruction. To evaluate the role of ADCC in prevention of new tumor implantation in vivo, female SCID mice (n=10-12 in each group) receive an intraperitoneal injection of either 20 mg/kg, 10 mg/kg, 5 mg/kg or 1 mg/kg IgG beginning 24 hours before tumor implantation and then twice each week for 4 weeks. Because it is expected that both antibodies are able to cause immunodepletion of the tumor cells, it is expected that this dose response comparison of the CHO and YB2/0 produced IgG1 Mabs is able to detect differences in the in vivo potency of the two Mabs. An isotype matched human IgG1 control Mab produced from the same cells will serve as controls (n=5-6 in each group). These procedures were repeated with additional cohorts of subjects comprising a total of 100-120 mice.

The ability of Mab1567 to destroy existing tumors in vivo is evaluated with the optimal dose of Mab1567 determined in the pre-implantation treatment model. In brief, one fixed and equal concentration of each Mab is used. The ability of the Mab to inhibit early and late tumor growth is evaluated. Specifically, on day +1 (early tumor) or day +5 (late tumor) after tumor implantation, female SCID mice (n=10-12 in each group) receive an intraperitoneal injection of a fixed and equal dose of CHO or YB2/0 Mab twice each week for 4 weeks. An isotype matched human IgG1 control Mab produced from the same cells serves as the control (n=5-6 in each group). It is anticipated that the results of this study are parallel to the results described above. In both models, monitoring of tumor growth by caliper measurements, Xenogen imaging in live animals and by histology and immunohistochemistry in sacrificed animals is performed as described in Examples 33 and 34. These procedures were repeated with additional cohorts of mice comprising a total of 60 subjects.

Following the conclusion of the above studies, the most potent antibody is chosen and the stable high secretor cell line is transferred to the National Cell Culture Core (NCCC). The NCCC is contracted to establish a non-GMP cell bank from the Parental Seed Stock of high-secretor CHO or YB2/0 cell line and to produce 20 grams cGLP grade Mab1567 for animal studies. Under contract, the cells are thawed, screened for mycoplasma (GLP), a 10 vial cell bank (GLP) is made, and production optimization work (media screening using the micro-bioreactor) is performed. Supernatant produced from the hollow fiber bioreactor is further processed using affinity chromatography to produce bulk purified antibody with low levels of endotoxin.

Example 42

Mab 1567-Mediated Immunodepletion of CCR4+ T Cells from the Peripheral Blood and Lymphoid Tissues of Non-Human Primates The cynomolgus monkey (*Macaca fascicularis*) is widely used as an animal model for analyzing immunity, hematopoiesis, infectious diseases, transplantation, and toxicology, because this macaque species is phylogenetically proximate to humans (Vugmeyster Y et al. Cytometry A 2003, 52:101-109; Vugmeyster Y. et al. Int Immunopharmacol 2003, 3:1477-1481). In particular, cynomolgus monkeys have been extensively used to study therapeutic agents aimed at B-cell depletion, such as anti-CD20 (Rituximab) (Reff M. E. et al. Blood 1994, 83:435-445) and anti-CD40 Mabs (Boon L. et al. Toxicology 2002, 174:53-65) and in preventing allograft rejection with anti-CTLA-4 (Palmisano G. L. et al. Clin Exp Immunol 2004, 135:259-266). Rhesus macaques (*Macaca mulatta*) have been infused with anti-CD80 (B7-1), anti-CD86 (B7-2) Mabs to assess allograft rejection as well (Vugmeyster Y et al. Cytometry A 2003, 52:101-109). To obtain additional data to support the hypothesis that Mab1567 can be used for the immunodepletion of CD4+/CCR4+ CTCLs, preliminary feasibility studies to assess the in vivo immunodepletion of CD4+/CCR4+ T-cells from peripheral blood (pb), bronchoalveolar lavage, bone marrow (BM), and lymphatic tissue are performed following systemic administration of Mab1567 in either cynomologus or rhesus macaques.

All studies are performed at the New England Primate Research Center. Macaques weighing 4-6 kg are used in the studies with one animal receiving each dose in the dose escalation studies. The most potent form of Mab1567, either CHO- or YB2/0-produced Mab, is used. Preliminary in vitro studies are performed to confirm that Mab1567 binds to CD4+/CCR4+ T cells by FACS staining. Subsequently, each animal receives a single dose infusion of Mab given intravenously corresponding to 0.05 mg/kg, 0.5 mg/kg, 1 mg/kg, 5 mg/kg and 10 mg/kg. An isotype-matched control Mab is given to four control animals at 10 mg/kg. Pre-treatment peripheral blood is obtained. Peripheral blood samples are also collected on days 1, 2, 4, 8, 15, 29, and subsequently thereafter at biweekly intervals until completion of the study on day 90. Lymph node biopsies from the inguinal nodes are taken at days 15 and 29 with cell preparations stained for quantification of lymphocyte populations by flow cytometry. Percent depletion of CD4+/CCR4+ in anti-CCR4 Mab treated animals is calculated by the formula: % depletion=100−% CD4+CCR4+ cells in treated lymph nodes divided by % CD4+/CCR4+ cells in control Mab treated animals. Other Mabs are used to assess the effect of anti-CCR4 Mab treatment on B cells (anti-CD20), T cell subsets (anti-CD3, CD4, CD8, CD45RA, CD45RO) including Tregs (CD25, FoxP3), macrophages (CD68, CD163), and others.

The immunophenotypic composition of bronchalveolar lavage cells is performed to evaluate the effect of Mab1567 on pulmonary immune cells. Briefly, animals are anesthetized with ketamine HCl and 0.4 mm diameter bronchoscope is used to infuse a 20 ml aliquot of sterile physiologic saline (PBS) (Hendricks E. E. et al. J Infect Dis 2004, 189:1714-1720). The fluid is removed and the procedure is repeated 3-4 times. The cells are pelleted and washed 3 times with PBS before staining with monoclonal antibodies and FACS analysis. Pre-treatment values are compared to samples taken on days 2, 8, and 29.

In order to evaluate alterations in the T cell composition of lymph nodes, macrophage activation, chemokine expression and chemokine receptor expression, immunohistochemistry is performed on formalin-fixed paraffin-embedded tissues and/or frozen tissue sections (Mansfield K. G. et al. Am J Pathol 2001, 159:693-702). Tissue sections are cut at 5 μm and immunostained using an avidin-biotin-horseradish peroxidase complex technique with a diaminobenzidine (DAB) chromogen. Sections are stained for the T cell markers CD3 (1.43 μg/ml, DAKO, Carpenteria, Calif.), CD8, CD4, the B cell marker CD20, macrophage markers CD68 and CD163, the MHC II molecule HLA-DR (clone CR3/43, 1.0 μg/ml, DAKO, Carpenteria, Calif.), the α-chemokine receptor CXCR3 (Clone 106, 0.33 μg/ml, BD Pharmingen, San Diego, Calif.), and the α-chemokine, monokine induced by INF-γ (MIG, 1.0 μg/ml, R&D Systems, Minneapolis, Minn.). Sections are examined with an Olympus Vanox-S AHBS microscope interfaced with a Leica QWin image analysis system (Leica Imaging Systems, Cambridge, UK) via a DEI 750 charge-coupled device camera (Optronics, Goleta, Calif.). Images of 10-20 random fields from each lymph node for each marker are captured at 400× magnification. Based on DAB chromogen staining, the area per lymph node that stains positive is used to calculate the percent area that was positive for each marker. This technique allows the quantitative analysis of immunomorphologic alterations in lymph node structure.

Example 43

Mab 1567-Mediated Lymphocyte Recruitment in a Delayed Hypersensitivity Model in Non-Human Primates The effect of Mab1567 on lymphocyte recruitment in a cutaneous delayed type hypersensitivity model is evaluated. Preliminary toxicology studies in the same non-human primate are also performed. As one example, studies on cynomolgus macaques are described below.

A cutaneous delayed type hypersensitivity model is used to examine the dose response to Mab1567 on the temporal recruitment of lymphocytes and macrophages. Briefly, animals are sensitized to mycobacterial antigens by intradermal injection of Complete Freunds Adjuvant 5-6 months prior to the initiation of the study (Silber A. et al. J Clin Invest 1994, 93:1554-1563). Following administration of the test or control antibody animals receive 0.1 ml of tuberculin made from standardized filtrates of *Mycobacterium tuberculosis* (Coopers Animal Health). Multiple intradermal injections are given along the dorsum and sites are biopsied under anesthesia at 0, 4, 8, 24, 48, 72, 96, 144, 168 and 264 hours after injection. Biopsies are split and snap frozen or fixed in 10% neutral buffered formalin for immunohistochemical analysis and quantitative image analysis. A total of four animals are evaluated with animals randomly receiving control or test antibody followed by a 1 month washout period and cross over to the remaining antibody. The dose to be evaluated is dependant on results of in vivo depletion studies described above.

Example 44

In Vivo Toxicology Studies

This protocol is designed to evaluate the toxicity (if any) associated with the administration of Mab 1567, as well as the efficacy of CD4+/CCR4+ depletion from lymph nodes and bone marrow. A weekly dosing regimen is adapted but the specific timing interval depends on the immunodepletion studies described above. In this study, four animals are given weekly doses of circa 15 mg/kg. At the completion of the dosing schedule, lymph node and BM specimens are obtained and analyzed by flow cytometry for the presence of CD4+/CCR4+ cells. Two animals are examined 22 days after the last dose and the other two are examined at 36 days. One control animal is euthanized and evaluated on day 22 and 36.

All animals used in the in vivo studies are evaluated daily for symptoms of toxicity by physical examination, which includes assessment of body temperature, weight loss, skin manifestations such as rashes and infections (due to critical role of skin homing CD4+/CCR4+ T cells), routine blood chemistry, and urinalysis. Two of the four animals in the multiple high-dose study are euthanized at the end of the study at 22 days after final dosing. At necropsy body tissues are thoroughly examined for evidences of toxicity and tissue damage. In addition to histologic analysis, lymph nodes, bone marrow, spleen, thymus and gastrointestinal tissue are obtained for lymphocyte isolation and analysis. Ex vivo pulmonary lavage is performed and cells are similarly isolated for FACS analysis. Finally immunohistochemistry with quantitative image analysis is performed to further characterize immunomorphologic changes.

It is expected that Mab1567 shows cross-reactivity against cynomolgus macaque CCR4 as it does with rhesus macaque CCR4 (FIG. 12). It is also expected that immunodepletion of CD4+/CCR4+ memory T-cells occurs. It is also possible that immunodepletion of Tregs occurs. Minimal immunogenicity of Mab1567 is expected because amino acid sequence analysis of the IgG heavy chain constant region locus has shown that the homology between these two non-human primates and humans is very high (>95%)[115,116]. Likewise, $V_{kappa}$ and $V_{lambda}$ variable region genes in macaques show 85 to 98% identify with the corresponding human variable region genes (Palmisano G. L. et al. Clin Exp Immunol 2004, 135:259-266; Hendricks E. E. et al. J Infect Dis 2004, 189:1714-1720). This degree of homology is indistinguishable from that observed between, for example, members of human immunoglobulins from the same gene family. However, this degree of similarity is formally tested by ELISA on anti-CCR4 Mab (anti-idiotype Ab response) verses isotype matched human IgG1 Mab (anti-isotype Ab response) coated plates using serum recovered from the animals.

Example 45

GMP Cell Bank and Manufacturing

Biovest is contracted to establish and perform safety testing on our cGMP Master Cell Banks. This service includes establishment of master cell bank (MBC) of 100 vials and master working cell banks (MWCB). cGMP testing per cell line is performed for mycoplasma, sterility, bacteriostasis/Fungistasis, adventitious virus and other virus testing Biovest also produces and purifies 5 grams cGMP Mab1567 for the pre-clinical tissue cross-reactivity and pharmacokinetic and toxicology studies in non-human primates and for the anticipated phase I/II clinical trial. The bulk purified material is similarly tested as above Charles River Laboratories is also contracted to perform stability testing as well as sterile filling of the product vials.

Example 46

Pharmacokinetic and Toxicology Studies in the Cynomolgus Macaque

These studies are performed under contact with Aptuit (formerly Quintiles-Edinburgh) using the cGMP Mab1567. These studies include a single dose acute toxicology study in the rat with a 14 day recovery Primate cyclic dose range and MTD dose studies are also performed. Importantly, a 7 cycle repeat dose toxicology study with toxicokinetic sampling with 28 days of recovery is conducted. This study is conducted in anticipation of the design of a repeat dosing phase II study. Indeed, several of the monoclonal antibodies in the clinic today for the treatment of non-Hodgkin's lymphoma (Rituximab, Campath) use multiple dosing (e.g. 5 doses) per cycle. A seven cycle study is conducted to provide a safety window for the anticipated design of our phase II study (e.g. five weekly doses per cycle).

Example 47

Full Human and Cynomolgus Macaque Tissue Cross-Reactivity Study with cGMP Mab1567

The studies are performed under GLP compliance. For the human studies, a full human tissue panel (up to 37 human tissues from each of three unrelated donors) is used with two concentrations of Mab1567 and one negative control article. For the macaque studies, up to 36 tissues from each of two donors are tested with two concentrations of the anti-CCR4 Mab and one negative control article. The stained tissue slides are evaluated by a board certified veterinary pathologist and reviewed by a second veterinary pathologist with similar qualifications Example 48

Figure 17:
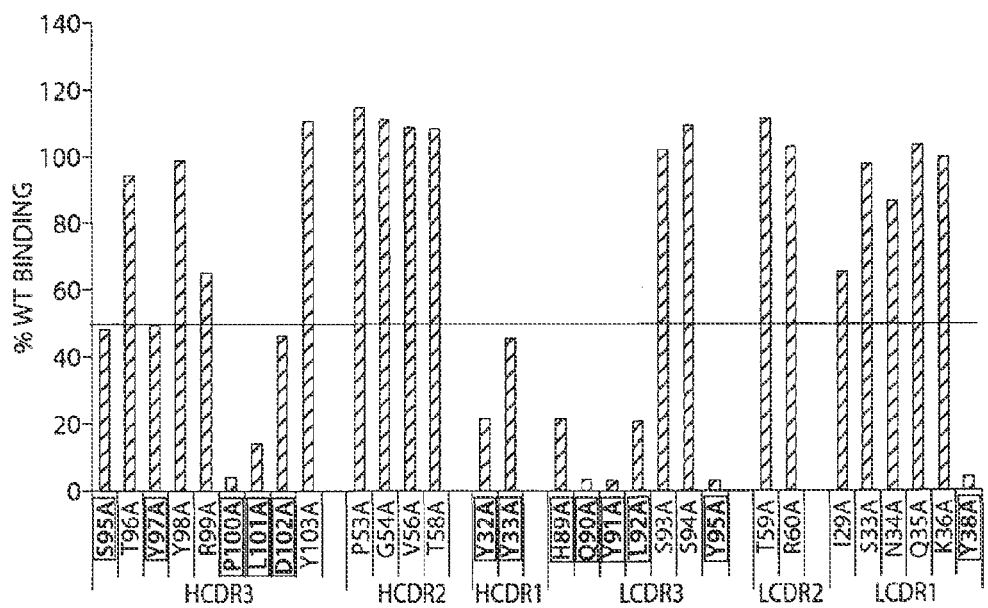
FIG. 17 is a graph showing alanine-scanning analysis of functional residues in the CDRs of humanized 1567 for binding to human CCR4 on cell surface.

Alanine-Scanning Analysis of Functional Residues in the CDRs of Humanized 1567 for Binding to Human CCR4 on Cell Surface FIG. 17 depicts a graph of percent wild type (WT) binding to 30 amino acids in the six CDRs of Ab 1567 were mutated to alanine. The humanized 1567 scFv-Fc construct (pcDNA3.1-scFv-Fc) was used as the template for mutagenesis using QuikChange method (Stratagene). Each mutant was expressed and purified as scFv-Fc antibody fragment. Their binding activity for CCR4+ Mac-1 cells was analyzed by FACS at various concentrations (3-fold serial dilution from 100 µg/mL, total 8 concentrations). Mean fluorescence intensity (MFI) of each mutant was normalized against wild type humanized 1567-scFv-Fc (100%). % binding of each mutant at concentration of 3.7 µg/mL was shown in the figure. Thirteen mutants (highlighted in pink) reduced binding to CCR4 greater than 50%. These residues are randomized to generate a library for affinity maturation of 1567.

The preceding study determined, in part, the following consensus sequences. The heavy chain CDRs of the huCCR4 antibody have the following consensus sequences, wherein X is meant to denote any natural, unnatural amino acid or amino acid analogue. For example, X is an alanine. In certain embodiments of the invention the heavy chain CDRs of the huCCR4 antibody have the following sequences: GYTFASYY (SEQ ID NO:5); WINXXNXNXKYNEKFKG (SEQ ID NO:11); and SXYXXPLDX (SEQ ID NO: 12). The light chain CDRs of the huCCR4 antibody have the following consensus sequences, wherein X is meant to denote any natural, unnatural amino acid or amino acid analogue. For example, X is an alanine. In certain embodiments of the invention the light chain CDRs of the huCCR4 antibody have the following sequences: KSSQSXLYSXXXXNYLA (SEQ ID NO: 13); WASXXES (SEQ ID NO: 14); and HQYLXXYT (SEQ ID NO: 15).

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of selectively killing a tumor cell comprising contacting said cell with a composition comprising a humanized monoclonal CC-chemokine receptor 4 (CCR4) antibody or fragment thereof, wherein said antibody has the following characteristics:
   a. binds to CCR4 positive (CCR4+) cells but not CCR4 negative (CCR4−) cells;
   b. decreases binding of a ligand or agonist to the CCR4 receptor; and wherein said antibody comprises
   i. a heavy chain variable region encoded by the nucleic acid sequence comprising:
      CAGGTGCAGCTGGTGCAGAGCGGAGCCGAGGTGAAGAAGCCTG GAGCTTCCGTCAAGGTGTCCTGCAAGGCCAGCGGCTACACCTTC GCCAGCTACTACATGCACTGGATGCGGCAGGCACCTGGACAGG GCCTCGAATGGATCGGCTGGATCAACCCCGGCAACGTGAACAC CAAGTACAACGAGAAGTTCAAGGGCAGGGCCACCCTGACCGTG GACACCAGCACCAACACCGCCTACATGGAACTGAGCAGCCTGC GGAGCGAGGACACCGCCGTGTACTACTGCGCCAGAAGCACCTA CTACCGGCCCCTGGACTACTGGGCCAGGGCACCCTGGTGACC GTGAGCAGC (SEQ ID NO:1); or
   ii. a heavy chain variable region comprising the amino acid sequence:
      QVQLVQSGAEVKKPGASVKVSCKASGYTFASYYMHWMRQAPG QGLEWIGWINPGNVNTKYNEKFKGRATLTVDTSTNTAYMELS SL RSEDTAVYYCARS TYYRPLDYWGQGTLVTVSS (SEQ ID NO:2); and
   iii. a light chain variable region encoded by the nucleic acid sequence comprising:
      GACATCGTGATGACCCAGAGCCCCGACAGCCTGGCCGTGAGCC TGGGCGAGCGGGCCACCATCAACTGCAAGAGCAGCCAGAGCA TCCTGTACAGCAGCAACCAGAAGAACTACCTGGCCTGGTATCA GCAGAAGCCCGGCCAGAGCCCCAAGCTGCTGATCTACTGGGCC AGCACCCGGGAGAGCGGCGTGCCCGACCGGTTTAGCGGCAGC GGCTCCGGCACCGACTTCACCCTGACCATCAGCAGCCTGCAGG CCGAGGACGTGGCCGTGTACTACTGCCACCAGTACCTGAGCAG CTACACCTTCGGCCAGGGCACAAAGCTGGAAATCAAG (SEQ ID NO:3); or
   iv. a light chain variable region comprising the amino acid sequence:
      DIVMTQSPDSLAVSLGERATINCKSSQSILYSSNQKNYLAWYQQKPG QSPKLLIYWASTRESGVPDRFSGSGSGTDFTLTISSLQAEDVAVYYC HQYLSSYTFGQGTKLEIK (SEQ ID NO:4).

2. The method of claim 1, wherein said selective killing occurs by antibody-dependent cellular toxicity (ADCC), complement-dependent cytotoxicity (CDC), antibody dependent cellular phagocytosis (ADCP).

3. The method of claim 1, wherein said tumor cell expresses CCR4.

4. The method of claim 1, wherein said tumor cell is a T-cell.

5. A method of decreasing suppressor T-cell activity comprising contacting said cell with a composition comprising a humanized monoclonal CC-chemokine receptor 4 (CCR4) antibody or fragment thereof, wherein said antibody has the following characteristics:
   a. binds to CCR4 positive (CCR4+) cells but not CCR4 negative (CCR4−) cells;
   b. decreases binding of a ligand or agonist to the CCR4 receptor; and wherein said antibody comprises
   i. a heavy chain variable region encoded by the nucleic acid sequence comprising:
      CAGGTGCAGCTGGTGCAGAGCGGAGCCGAGGTGAAGAAGCCTG GAGCTTCCGTCAAGGTGTCCTGCAAGGCCAGCGGCTACACCTTC GCCAGCTACTACATGCACTGGATGCGGCAGGCACCTGGACAGG GCCTCGAATGGATCGGCTGGATCAACCCCGGCAACGTGAACAC CAAGTACAACGAGAAGTTCAAGGGCAGGGCCACCCTGACCGTG GACACCAGCACCAACACCGCCTACATGGAACTGAGCAGCCTGC GGAGCGAGGACACCGCCGTGTACTACTGCGCCAGAAGCACCTA CTACCGGCCCCTGGACTACTGGGGCCAGGGCACCCTGGTGACC GTGAGCAGC (SEQ ID NO:1); or
   ii. a heavy chain variable region comprising the amino acid sequence:
      QVQLVQSGAEVKKPGASVKVSCKASGYTFASYYMHWMRQAPG QGLEWIGWINPGNVNTKYNEKFKGRATLTVDTSTNTAYMELS SL RSEDTAVYYCARS TYYRPLDYWGQGTLVTVSS (SEQ ID NO:2); and
   iii. a light chain variable region encoded by the nucleic acid sequence comprising:
      GACATCGTGATGACCCAGAGCCCCGACAGCCTGGCCGTGAGCC TGGGCGAGCGGGCCACCATCAACTGCAAGAGCAGCCAGAGCA TCCTGTACAGCAGCAACCAGAAGAACTACCTGGCCTGGTATCA GCAGAAGCCCGGCCAGAGCCCCAAGCTGCTGATCTACTGGGCC AGCACCCGGGAGAGCGGCGTGCCCGACCGGTTTAGCGGCAGC GGCTCCGGCACCGACTTCACCCTGACCATCAGCAGCCTGCAGG CCGAGGACGTGGCCGTGTACTACTGCCACCAGTACCTGAGCAG CTACACCTTCGGCCAGGGCACAAAGCTGGAAATCAAG (SEQID NO:3); or
   iv. a light chain variable region comprising the amino acid sequence:
      DIVMTQSPDSLAVSLGERATINCKSSQSILYSSNQKNYLAWYQQKPG QSPKLLIYWASTRESGVPDRFSGSGSGTDFTLTISSLQAEDVAVYYC HQYLSSYTFGQGTKLEIK (SEQ ID NO:4).

6. A method of augmenting an immune response to an antigen comprising contacting said cell with a composition comprising a humanized monoclonal CC-chemokine receptor 4 (CCR4) antibody or fragment thereof, wherein said antibody has the following characteristics:
   a. binds to CCR4 positive (CCR4+) cells but not CCR4 negative (CCR4−) cells;
   b. decreases binding of a ligand or agonist to the CCR4 receptor; and wherein said antibody comprises
   i. a heavy chain variable region encoded by the nucleic acid sequence comprising:
      CAGGTGCAGCTGGTGCAGAGCGGAGCCGAGGTGAAGAAGCCTG GAGCTTCCGTCAAGGTGTCCTGCAAGGCCAGCGGCTACACCTTC GCCAGCTACTACATGCACTGGATGCGGCAGGCACCTGGACAGG GCCTCGAATGGATCGGCTGGATCAACCCCGGCAACGTGAACAC CAAGTACAACGAGAAGTTCAAGGGCAGGGCCACCCTGACCGTG GACACCAGCACCAACACCGCCTACATGGAACTGAGCAGCCTGC GGAGCGAGGACACCGCCGTGTACTACTGCGCCAGAAGCACCTA CTACCGGCCCCTGGACTACTGGGGCCAGGGCACCCTGGTGACC GTGAGCAGC (SEQ ID NO:1); or
   ii. a heavy chain variable region comprising the amino acid sequence:
      QVQLVQSGAEVKKPGASVKVSCKASGYTFASYYMHWMRQAPG QGLEWIGWINPGNVNTKYNEKFKGRATLTVDTSTNTAYMELS SL RSEDTAVYYCARS TYYRPLDYWGQGTLVTVSS (SEQ ID NO:2); and
   iii. a light chain variable region encoded by the nucleic acid sequence comprising:
      GACATCGTGATGACCCAGAGCCCCGACAGCCTGGCCGTGAGCC TGGGCGAGCGGGCCACCATCAACTGCAAGAGCAGCCAGAGCA TCCTGTACAGCAGCAACCAGAAGAACTACCTGGCCTGGTATCA GCAGAAGCCCGGCCAGAGCCCCAAGCTGCTGATCTACTGGGCC AGCACCCGGGAGAGCGGCGTGCCCGACCGGTTTAGCGGCAGC GGCTCCGGCACCGACTTCACCCTGACCATCAGCAGCCTGCAGG CCGAGGACGTGGCCGTGTACTACTGCCACCAGTACCTGAGCAG CTACACCTTCGGCCAGGGCACAAAGCTGGAAATCAAG (SEQID NO:3); or
   iv. a light chain variable region comprising the amino acid sequence:
      DIVMTQSPDSLAVSLGERATINCKSSQSILYSSNQKNYLAWYQQKPG QSPKLLIYWASTRESGVPDRFSGSGSGTDFTLTISSLQAEDVAVYYC HQYLSSYTFGQGTKLEIK (SEQ ID NO:4).

7. The method of claim 6, wherein said antigen is a viral antigen, a bacterial antigen or a tumor associated antigen.

8. The method of claim 7, wherein said viral antigen is HIV.

9. The method of claim 6, wherein said antibody is administered prior to or after exposure to the antigen.

10. The method of claim 6, wherein said administration of said antibody causes an increase in antigen specific T cell activity.

11. The method of claim 10, wherein said T-cell is an effector T-cell.

12. A method of increasing vaccine efficiency comprising administering to a subject a vaccine and a composition comprising a humanized monoclonal CC-chemokine receptor 4 (CCR4) antibody or fragment thereof, wherein said antibody has the following characteristics:
   a. binds to CCR4 positive (CCR4+) cells but not CCR4 negative (CCR4−) cells;

b. decreases binding of a ligand or agonist to the CCR4 receptor; and wherein said antibody comprises
i. a heavy chain variable region encoded by the nucleic acid sequence comprising:
CAGGTGCAGCTGGTGCAGAGCGGAGCCGAGGTGAAGAAGCCTG GAGCTTCCGTCAAGGTGTCCTGCAAGGCCAGCGGCTACACCTTC GCCAGCTACTACATGCACTGGATGCGGCAGGCACCTGGACAGG GCCTCGAATGGATCGGCTGGATCAACCCCGGCAACGTGAACAC CAAGTACAACGAGAAGTTCAAGGGCAGGGCCACCCTGACCGTG GACACCAGCACCAACACCGCCTACATGGAACTGAGCAGCCTGC GGAGCGAGGACACCGCCGTGTACTACTGCGCCAGAAGCACCTA CTACCGGCCCCTGGACTACTGGGCCAGGGCACCCTGGTGACC GTGAGCAGC (SEQ ID NO:1); or
ii. a heavy chain variable region comprising the amino acid sequence:
QVQLVQSGAEVKKPGASVKVSCKASGYTFASYYMHWMRQAPG QGLEWIGWINPGNVNTKYNEKFKGRATLTVDTSTNTAYMELS SL RSEDTAVYYCARS TYYRPLDYWGQGTLVTVSS (SEQ ID NO:2); and
iii. a light chain variable region encoded by the nucleic acid sequence comprising:
GACATCGTGATGACCCAGAGCCCCGACAGCCTGGCCGTGAGCC TGGGCGAGCGGGCCACCATCAACTGCAAGAGCAGCCAGAGCA TCCTGTACAGCAGCAACCAGAAGAACTACCTGGCCTGGTATCA GCAGAAGCCCGGCCAGAGCCCCAAGCTGCTGATCTACTGGGCC AGCACCCGGGAGAGCGGCGTGCCCGACCGGTTTAGCGGCAGC GGCTCCGGCACCGACTTCACCCTGACCATCAGCAGCCTGCAGG CCGAGGACGTGGCCGTGTACTACTGCCACCAGTACCTGAGCAG CTACACCTTCGGCCAGGGCACAAAGCTGGAAATCAAG (SEQID NO:3); or
iv. a light chain variable region comprising the amino acid sequence:
DIVMTQSPDSLAVSLGERATINCKSSQSILYSSNQKNYLAWYQQKPG QSPKLLIYWASTRESGVPDRFSGSGSGTDFTLTISSLQAEDVAVYYC HQYLSSYTFGQGTKLEIK (SEQ ID NO:4).

13. The method of claim 12 wherein said antibody and said vaccine are administered sequentially or concurrently.

14. The method of claim 12, wherein said vaccine is a tumor vaccine, a bacterial vaccine, or a viral vaccine.

15. A method of treating or alleviating a symptom of cancer, comprising administering to a subject in need thereof a composition comprising an humanized monoclonal CC-chemokine receptor 4 (CCR4) antibody or fragment thereof, wherein said antibody has the following characteristics:
a. binds to CCR4 positive (CCR4+) cells but not CCR4 negative (CCR4−) cells;
b. decreases binding of a ligand or agonist to the CCR4 receptor; and wherein said antibody comprises
i. a heavy chain variable region encoded by the nucleic acid sequence comprising:
CAGGTGCAGCTGGTGCAGAGCGGAGCCGAGGTGAAGAAGCCT GGAGCTTCCGTCAAGGTGTCCTGCAAGGCCAGCGGCTACACCT TCGCCAGCTACTACATGCACTGGATGCGGCAGGCACCTGGAC AGGGCCTCGAATGGATCGGCTGGATCAACCCCGGCAACGTGA ACACCAAGTACAACGAGAAGTTCAAGGGCAGGGCCACCCTGA CCGTGGACACCAGCACCAACACCGCCTACATGGAACTGAGCA GCCTGCGGAGCGAGGACACCGCCGTGTACTACTGCGCCAGAA GCACCTACTACCGGCCCCTGGACTACTGGGGCCAGGGCACCCT GGTGACCGTGAGCAGC (SEQ ID NO:1); or
ii. a heavy chain variable region comprising the amino acid sequence:
QVQLVQSGAEVKKPGASVKVSCKASGYTFASYYMHWMRQAPG QGLEWIGWINPGNVNTKYNEKFKGRATLTVDTSTNTAYMELS SL RSEDTAVYYCARS TYYRPLDYWGQGTLVTVSS (SEQ ID NO:2); and
iii. a light chain variable region encoded by the nucleic acid sequence comprising:
GACATCGTGATGACCCAGAGCCCCGACAGCCTGGCCGTGAGCC TGGGCGAGCGGGCCACCATCAACTGCAAGAGCAGCCAGAGCA TCCTGTACAGCAGCAACCAGAAGAACTACCTGGCCTGGTATCA GCAGAAGCCCGGCCAGAGCCCCAAGCTGCTGATCTACTGGGCC AGCACCCGGGAGAGCGGCGTGCCCGACCGGTTTAGCGGCAGC GGCTCCGGCACCGACTTCACCCTGACCATCAGCAGCCTGCAGG CCGAGGACGTGGCCGTGTACTACTGCCACCAGTACCTGAGCAG CTACACCTTCGGCCAGGGCACAAAGCTGGAAATCAAG (SEQID NO:3); or
iv. a light chain variable region comprising the amino acid sequence:
DIVMTQSPDSLAVSLGERATINCKSSQSILYSSNQKNYLAWYQQKPG QSPKLLIYWASTRESGVPDRFSGSGSGTDFTLTISSLQAEDVAVYYC HQYLSSYTFGQGTKLEIK (SEQ ID NO:4).

16. The method of claim 15, wherein said cancer is a solid cancer or a hematologic cancer.

17. The method of claim 16, wherein said hematologic cancer is cutaneous T-cell Lymphoma (CTCL), mycosis fungoides (MF), primary cutaneous anaplastic large cell Lymphoma (cutaneous ALCL), Sezary syndrome, or adult T cell Leukemia/Lymphoma (ATLL).

18. The method of claim 16, where said solid cancer is breast cancer, lung cancer, ovarian cancer, prostate cancer, colon cancer, cervical cancer, brain cancer, liver cancer, pancreatic cancer, kidney or stomach cancer.

* * * * *